(12) United States Patent
Padmanabhan et al.

(10) Patent No.: US 7,793,410 B2
(45) Date of Patent: Sep. 14, 2010

(54) METHOD OF MAKING A PLURALITY OF FLOW SENSORS

(75) Inventors: Aravind Padmanabhan, Plymouth, MN (US); Ulrich Bonne, Hopkins, MN (US); Michael G. Marchini, Freeport, IL (US)

(73) Assignee: Honeywell International Inc., Morristown, NJ (US)

( * ) Notice: Subject to any disclaimer, the term of this patent is extended or adjusted under 35 U.S.C. 154(b) by 61 days.

(21) Appl. No.: 11/781,197

(22) Filed: Jul. 20, 2007

(65) Prior Publication Data

US 2008/0010821 A1 Jan. 17, 2008

Related U.S. Application Data

(60) Division of application No. 10/930,546, filed on Aug. 31, 2004, now Pat. No. 7,258,003, which is a continuation-in-part of application No. 10/128,775, filed on Apr. 22, 2002, now Pat. No. 6,911,894, which is a continuation-in-part of application No. 09/656,694, filed on Sep. 7, 2000, now Pat. No. 7,109,842, which is a continuation-in-part of application No. 09/207,165, filed on Dec. 7, 1998, now Pat. No. 6,184,773, and a continuation-in-part of application No. 09/368,621, filed on Aug. 5, 1999, now Pat. No. 6,322,247, which is a continuation-in-part of application No. 09/239,125, filed on Jan. 28, 1999, now Pat. No. 6,361,206.

(51) Int. Cl.
*H05K 3/30* (2006.01)

(52) U.S. Cl. .................... 29/832; 29/417; 29/825; 29/835; 73/204.13; 73/204.22; 73/204.25; 73/204.26

(58) Field of Classification Search ............... 29/832, 29/417, 825, 835, 842, 856, 876; 73/195, 73/204.12, 204.13, 204.21, 204.22, 204.25, 73/204.26

See application file for complete search history.

(56) References Cited

U.S. PATENT DOCUMENTS 3,954,590 A    5/1976    Czuha, Jr.

(Continued)

FOREIGN PATENT DOCUMENTS

JP    3261825    11/1991

(Continued)

OTHER PUBLICATIONS

All Articles and Foreign Patents Cited in Previously Filed Parent U.S. Appl. No. 10/930,546, filed Aug. 31, 2004.

(Continued)

*Primary Examiner*—Thiem Phan
(74) *Attorney, Agent, or Firm*—Crompton Seager & Tufte LLC

(57) ABSTRACT

A method of making a plurality of flow sensors is provided, each flow sensor having a substrate with a sensing element and flow channel aligned over the sensing element. The sensing element senses at least one property of a fluid. The flow channel is aligned by one or more guide elements formed in an alignment layer. The flow channel across the sensing area is accurately and precisely aligned due to the guide elements provided at the wafer-level, facilitating reliable, low-cost, and consistent results among multiple flow sensors. The flow sensor is adapted for use in harsh environments.

19 Claims, 16 Drawing Sheets

U.S. PATENT DOCUMENTS

| | | | |
|---|---|---|---|
| 4,304,128 A | 12/1981 | Hafner et al. | |
| 4,343,768 A | 8/1982 | Kimura | |
| 4,472,239 A | 9/1984 | Johnson et al. | |
| 4,478,076 A | 10/1984 | Bohrer | |
| 4,478,077 A | 10/1984 | Bohrer et al. | |
| 4,501,144 A | 2/1985 | Higashi et al. | |
| 4,548,078 A | 10/1985 | Bohrer et al. | |
| 4,555,939 A | 12/1985 | Bohrer et al. | |
| 4,566,320 A | 1/1986 | Bohrer | |
| 4,571,608 A | 2/1986 | Johnson | |
| 4,581,928 A | 4/1986 | Johnson | |
| 4,587,105 A | 5/1986 | Bonne et al. | |
| 4,624,137 A | 11/1986 | Johnson et al. | |
| 4,651,564 A | 3/1987 | Johnson et al. | |
| 4,682,503 A | 7/1987 | Higashi et al. | |
| 4,683,159 A | 7/1987 | Bohrer et al. | |
| 4,696,188 A | 9/1987 | Higashi | |
| 4,706,061 A | 11/1987 | Johnson | |
| 4,708,636 A | 11/1987 | Johnson | |
| 4,733,559 A * | 3/1988 | Aine et al. | 73/195 |
| 4,739,657 A | 4/1988 | Higashi et al. | |
| 4,794,048 A | 12/1988 | Oboodi et al. | |
| 4,825,693 A | 5/1989 | Bohrer et al. | |
| 4,829,818 A | 5/1989 | Bohrer | |
| 4,856,328 A | 8/1989 | Johnson | |
| 4,867,842 A | 9/1989 | Bohrer et al. | |
| 4,885,938 A | 12/1989 | Higashi | |
| 4,891,977 A | 1/1990 | Johnson et al. | |
| 4,895,616 A | 1/1990 | Higashi et al. | |
| 4,914,742 A | 4/1990 | Higashi et al. | |
| 4,914,947 A | 4/1990 | Davidson | |
| 4,966,037 A | 10/1990 | Sumner et al. | |
| 5,081,866 A | 1/1992 | Ochiai et al. | |
| 5,237,523 A | 8/1993 | Bonne et al. | |
| 5,279,155 A | 1/1994 | Johnson et al. | |
| 5,311,447 A | 5/1994 | Bonne | |
| 5,410,916 A | 5/1995 | Cook | |
| 5,462,525 A | 10/1995 | Srisathapat et al. | |
| 5,521,123 A * | 5/1996 | Komatsu et al. | 438/64 |
| 5,684,253 A | 11/1997 | Bonne et al. | |
| 5,852,239 A | 12/1998 | Sato et al. | |
| 5,852,247 A | 12/1998 | Batey | |
| 5,869,749 A | 2/1999 | Bonne et al. | |
| 5,886,249 A | 3/1999 | Bonne et al. | |
| 5,965,812 A | 10/1999 | Manaka | |
| 6,023,969 A | 2/2000 | Feller | |
| 6,073,482 A | 6/2000 | Moles | |
| 6,079,264 A | 6/2000 | Yamakawa et al. | |
| 6,112,591 A | 9/2000 | Manaka | |
| 6,159,620 A | 12/2000 | Heath et al. | |
| 6,169,965 B1 | 1/2001 | Kubisiak et al. | |
| 6,184,773 B1 | 2/2001 | Bonne et al. | |
| 6,220,079 B1 | 4/2001 | Taylor et al. | |
| 6,223,593 B1 | 5/2001 | Kubisiak et al. | |
| 6,290,685 B1 | 9/2001 | Insley | |
| 6,308,553 B1 | 10/2001 | Bonne et al. | |
| 6,322,247 B1 | 11/2001 | Bonne et al. | |
| 6,336,361 B1 | 1/2002 | Uramachi et al. | |
| 6,361,206 B1 | 3/2002 | Bonne | |
| 6,472,459 B2 | 10/2002 | Morales et al. | |
| 6,502,459 B1 | 1/2003 | Bonne et al. | |
| 6,591,674 B2 | 7/2003 | Gehman et al. | |
| 6,665,207 B2 | 12/2003 | Wald et al. | |
| 6,681,623 B2 | 1/2004 | Bonne et al. | |
| 6,686,184 B1 | 2/2004 | Anderson et al. | |
| 6,710,311 B2 | 3/2004 | Villa et al. | |
| 6,732,583 B1 | 5/2004 | Yasuda et al. | |
| 6,924,087 B2 | 8/2005 | Yeshurun et al. | |
| 2003/0098771 A1 | 5/2003 | Padmanabhan et al. | |

FOREIGN PATENT DOCUMENTS

| | | |
|---|---|---|
| WO | 8700917 | 2/1987 |
| WO | 0107903 | 2/2001 |
| WO | 0111322 | 2/2001 |
| WO | 0184087 | 11/2001 |

OTHER PUBLICATIONS

Brooks Institute, "High Performance Metal Sealed Mass Flow Controller," Design Specification DS-5964, Hatfield, PA, pp. 1-4, Nov. 1998.

* cited by examiner

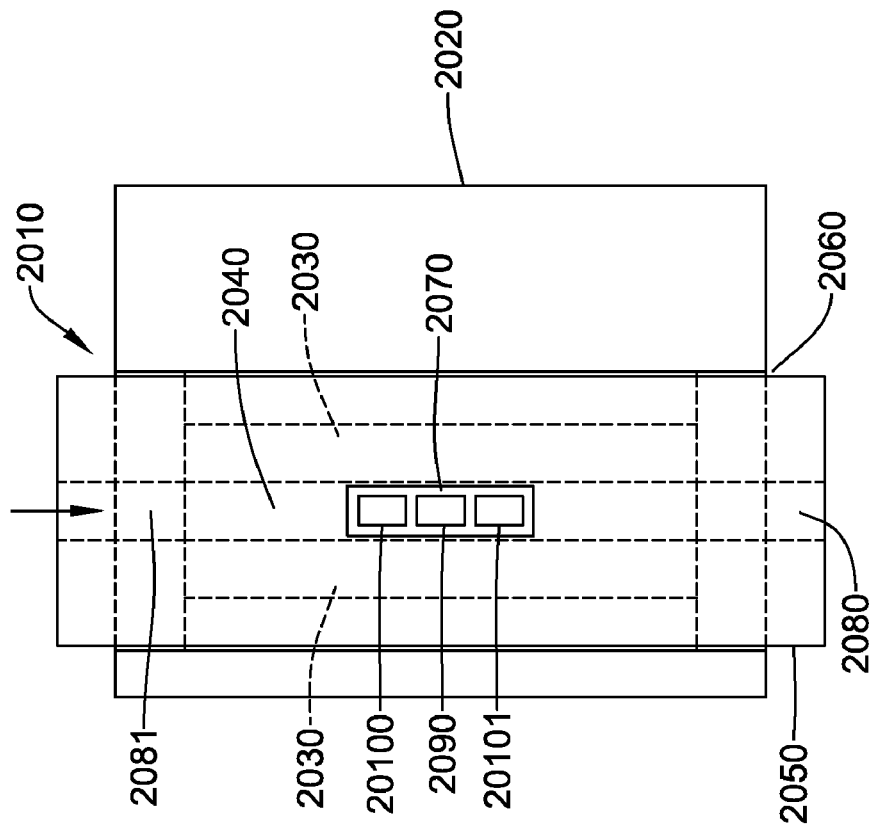
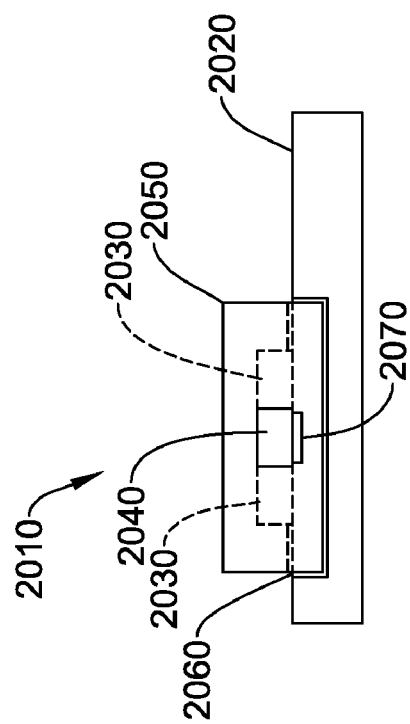
Figure 11B
Figure 11A

METHOD OF MAKING A PLURALITY OF FLOW SENSORS

This is a divisional of U.S. patent application Ser. No. 10/930,546, filed Aug. 31, 2004, entitled "Flow Sensor With Self-Aligned Flow Channel," which is a continuation-in-part of U.S. patent application Ser. No. 10/128,775, filed Apr. 22, 2002, entitled "Sensor Package for Harsh Environments", now U.S. Pat. No. 6,911,894, which is a continuation-in-part of U.S. patent application Ser. No. 09/656,694, filed Sep. 7, 2000, entitled "Robust Fluid Flow and Property Microsensor Made of Optimal Material," now U.S. Pat. No. 7,109,842, which is a continuation-in-part of U.S. patent application Ser. No. 09/207,165, filed Dec. 7, 1998, entitled "Rugged Fluid Flow and Property Microsensor," now U.S. Pat. No. 6,184,773, and U.S. patent application Ser. No. 09/368,621, filed Aug. 5, 1999, which is a Continuation-in-Part of U.S. patent application Ser. No. 09/239,125, filed Jan. 28, 1999, both entitled "Microsensor Housing," now U.S. Pat. Nos. 6,322,247 and 6,361,206 respectively. The content of the foregoing patent applications and patents are hereby incorporated by reference.

FIELD OF THE INVENTION

The present invention relates generally to sensors utilized to detect the quality and movement of fluids, in either gaseous or liquid form. The present invention relates more particularly to thermal sensors of such fluids, such as fluid flow or property sensors implemented on silicon, glass, quartz, or other substrates in microstructure form. The present invention relates to sensor packages for harsh environments. The invention relates to the alignment of a flow path over a sensing area.

BACKGROUND

Flow sensors are utilized in a variety of fluid-sensing applications for detecting the movement of fluids, which may be in gaseous of liquid form. One type of flow measurement, for example, is based on thermal sensors, which can be utilized to detect the properties of a fluid. Thermal sensors may be implemented, for example, over a silicon substrate in microstructure form. For convenience sake, and without limitation, the term "flow sensor" can be utilized to refer to such thermal sensors. (See e.g. U.S. Pat. No. 6,322,247 FIGS. 10a-f, and U.S. Pat. No. 6,184,773, which are both incorporated herein by reference.). The reader will appreciate that such sensors may also be utilized to measure intrinsic fluid properties such as thermal conductivity, specific heat (e.g. U.S. Pat. Nos. 5,237,523 and 5,311,447, which are both incorporated herein by reference.), non-intrinsic properties such as temperature, flow velocity, flow rate, and pressure, and other properties; and that the flows may be generated through forced or natural convection.

A thermal-type flow sensor can be formed from a substrate that includes a heating element and one or more heat-receiving, or sensing, elements. If two such sensing elements are utilized, they can be positioned at the upstream and downstream sides of the heating element relative to the direction of the fluid (liquid or gas) flow to be measured. When fluid flows along the substrate, it is heated by the heating element at the upstream side and the heat is then transferred non-symmetrically to the heat-receiving elements on either side of the heating element. Since the level of non-symmetry depends on the rate of fluid flow, and that non-symmetry can be sensed electronically, such a flow sensor can be used to determine the rate and the cumulative amount of the fluid flow.

Such flow sensors generally face potential degradation problems when exposed to harsh (e.g., contaminated, dirty, condensing, etc.) fluids, including gases or liquids that can "stress" the sensor via corrosion, radioactive or bacterial contamination, overheating, deposits or freeze-ups. The sensitive measurement of the flow, or pressure (differential or absolute) of "harsh" gases or liquids that can stress, corrode, freeze-up, or overheat the sensing elements is a challenge that is either unmet or met at great expense. Among the solutions proposed previously are passivation with the associated desensitization of the sensor, heaters to raise the temperature of gaseous fluids to be measured to avoid condensation or freeze-ups (or coolers to prevent overheating) at the expense of sensor signal degradation, cost increase and possible fluid degradation, or filters to remove objectionable particulate matter. Frequent cleaning or replacement and recalibration of the sensors are additional, but costly, solutions. Sensitive, membrane-based differential pressure sensors can be protected against contamination because no flow is involved, but they are less sensitive, typically cover a smaller flow range and are more expensive than thermal microsensors, in addition to not being overpressure proof.

The measurement of liquid flow via thermal microsensors, especially of electrically conductive fluids, thus presents challenging problems in terms of electrical insulation, flow noise, chip corrosion, potential for leaks or structural integrity of the flow channel, and thermal measurement. The electrical contacts to the sensor chip generally should be insulated from each other so the resistance to electrical leakage is above approximately 20 M$\Omega$ to avoid interference with the sensing function. Some $Si_3N_4$ passivation films, for example, have pinholes; spin-on coatings of compounds that form glass or Teflon® films upon curing have not shown insulation beyond a few days of contact with salt water. (Note that Teflon® is a registered trademark of the E.I. Du Pont De Nemours & Company Corporation of 101 West 101 West $10^{th}$St., Wilmington, Del. 19898.) Even potting the wire-bonds in highly cross-linked epoxy led to either resistances dropping to, for example, 30M$\Omega$ and/or bond breakage if the epoxy became too brittle due to excessive cross-linking and/or thermal cycling. Additionally, an odd shape of the flow channel above the chip causes extra turbulence and corresponding signal noise. Another approach to providing electrical insulation for the electrical contacts and leadout wires is to move them out of the fluid-flow channel and contact area; however, such sidewise displacement adds real estate to the chip size and therefore to its cost.

Regarding structural integrity, a sensitive 1 µm-thick flow sensing membrane can easily break as a result of the stronger viscous and inertial forces that a liquid can exert on it. Such breakage has even been observed in cases of sharp gaseous pressure or flow pulses. Finally, with respect to thermal measurement issues, the heater temperature rise typically permissible in liquids (e.g., $\leq 20°$ C.) is much smaller than the one typically utilized in gases (e.g., 100-160° C.). The resulting, relatively small signal causes more significant increases in the effect of composition-, sensor-material- and temperature-dependent offsets, which can cause significant errors in the sensor flow readouts.

Based on the foregoing, the present inventors have concluded that a solution to the aforementioned problems lies appropriately in the "smart" application onto the sensing chip of a film that is strong enough to function as a protective barrier to the transfer of electrical charges and of molecular mass transfer but can be thin enough to enable transfer of heat to allow thermal measurements. The films may be fashioned of materials composed of inorganic compounds (even metals)

or of hydrophobic or hydrophilic polymeric materials, as explained in further detail herein, which can result in operational flow sensors of high reliability, no electrical leakage, no fluid leakage by virtue of the non-intrusive character of the flow measurement, no corrosion, no fluid contamination, reduced flow noise and significantly reduced offset and drift problems.

Another challenge in the design and manufacture of flow sensors is the alignment of the fluid flow path across the sensing element. Precise and accurate alignment is necessary to achieve optimal performance of the sensor. Such precise alignment of sensors generally requires components of each sensor to be individually aligned, which is labor intensive and expensive. Time and cost in manufacturing flow sensors is greatly reduced when more of the production steps are completed while the sensors are at the wafer level. The present invention provides a solution to aligning the flow path precisely when the microsensors are at the wafer level.

SUMMARY OF THE INVENTION

The present invention provides a thermal sensor utilized in the detection of the quality or properties of fluids, including gas and liquid. The thermal sensor can be implemented on silicon, glass, quartz, or other substrates in microstructure form.

In one embodiment, the flow sensor has a substrate with a sensing element, one or more guide elements, and a flow channel; wherein the guide elements align the flow channel over the sensing element. The sensing element senses at least one property of a fluid. In a further embodiment, first and second guide elements define the flow channel. The present flow sensor provides a sensor in which the flow path across the sensing area is accurately and precisely aligned, facilitating reliable and consistent results among multiple flow sensors.

In another embodiment of the invention, a molded element defining one or more flow channel extensions is positioned over the guide elements, with the flow channel extensions in fluid communication with the flow channel. The combination of the flow channel and flow channel extensions define a fluid flow path over the sensing element. The molded element can form the top of the fluid flow path, or a cap can be attached to the molded element to form the top of the fluid flow path. In another embodiment of the invention, the flow sensor includes a substrate with a sensing element, an alignment layer deposited on the substrate and defining a location channel aligned over the sensing element, and a flow tube positioned within the location channel.

A method is provided for making a plurality of flow sensors each having a flow channel aligned with a sensing element. The method involves providing a substrate with a plurality of sensing elements aligned in a pattern, depositing a polymer layer onto the substrate and forming a plurality of guide elements in the polymer layer, with the guide elements positioned to align flow channels over a sensing element. In some embodiments, the guide elements form the flow channels. The substrate is then cut or diced into a plurality of pieces or chips, with each piece having a flow channel precisely aligned over a sensing element.

In yet another embodiment of the present invention, an apparatus is disclosed herein for detecting liquid flow in what may generically be referred to as a "harsh environment", in which toxic or corrosive fluids are analyzed. This embodiment can also be used for sensing pure or super-clean fluids, such that their contact with the sensor does not result in any detectable contamination of the fluid or adverse effects to the sensor. This improvement results from the sensor being isolated from the fluid flow path.

A sensor can be configured to generally include a flow channel block having a flow channel formed therein. The sensor additionally includes a substrate fastened to a sensor chip and contacted by at least one bonding element and a molded core tube inserted into the flow channel of the flow channel block, which thereby reduces flow noise and potential corrosion, improves electrical insulation, structural integrity and thermal measurements thereof derived from the sensor chip.

BRIEF DESCRIPTION OF THE DRAWINGS

The accompanying figures, like reference numerals refer to identical or functionally similar elements throughout the separate views.

FIGS. 11A and 11B are front and top views, respectively, of a microsensor assembly with an alignment layer according to the invention;

DETAILED DESCRIPTION

Figure 1:
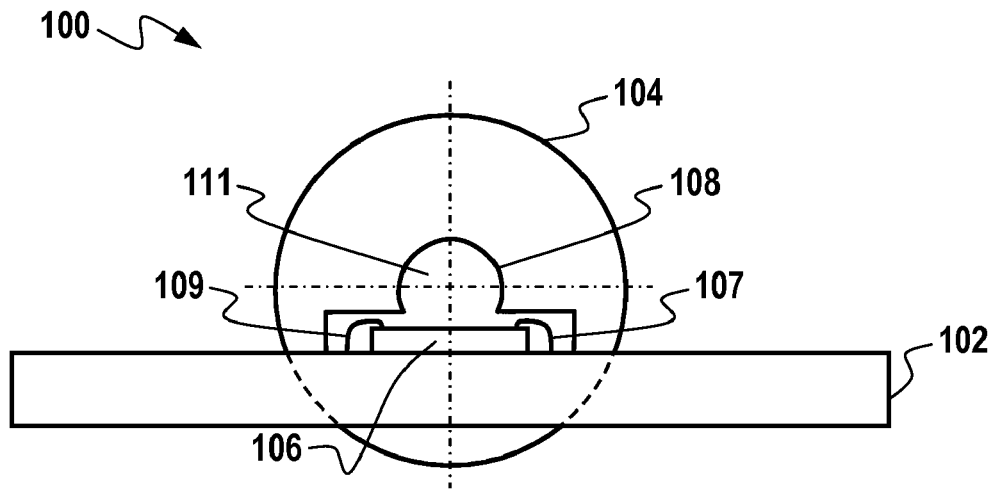
FIG. 1 illustrates a prior art cross-sectional view of a flow channel block.

The particular values and configurations discussed in these non-limiting examples can be varied and are cited merely to illustrate various embodiments of the present invention and are not intended to limit the scope of the invention.

One aspect of the present invention is related to the design and fabrication of the electrical insulation for electrical contacts to sensor chips using either front-wire-bond (FWB) or through-the-wafer (TTW) contacts of certain thermal flow microsensors or of environmental sensors in general. The present inventors previously insulated Au-wires and Au-pads of FWB sensor chips via materials, such as, for example, dip-coatings, dip-coatings with or without alumina thin-film undercoating, $Si_3N_4$, flowable sealants, solvent-resistant sealant with fluoro-silicon, and epoxies. Insulation based on such materials has been attempted as defined generally by the resistances between the sensing elements and the liquid (e.g., salt water) in a flow tube. Such resistances, however, are unacceptable if $\leq 20$ M$\Omega$. The invention described herein thus introduces a unique solution for solving such problems.

As will be explained in further detail herein, by potting insulating material (e.g., epoxy) around a core-mold of Teflon® wire or pipe of 0.010 to 0.060" OD, which may or may not be removed after curing, and using for example, a robust microbrick or an epoxy-back-filled microbridge, the aforementioned problems can be essentially eliminated. The increased thickness of the insulating "layer", relative to a dip-coat for example, causes the intrusion of fluids (e.g., water) and other conductive materials, such that their contribution to electrical conduction in the polymer becomes negligible. A straight and smooth flow channel, which can reduce turbulence and flow noise, thus replaces the old flow channel spaces located above previously utilized sensor chips.

Replacing an unprotected microbridge by a microbrick chip can eliminate breakage due to fluid-generated forces. Note that the utilization of a microbrick chip or other such devices are not considered limiting features of the present invention but are mentioned herein for illustrative and general edification purposes only. The increased insulation thickness enables the application of larger voltages to the sensor heating elements, which raises the heater temperature (which may or may not be in direct contact with the liquid) and leads to larger output signals. As a result, heater resistance drift, and temperature-, fluid-type-, sensor-asymmetry-, and electronics-dependent offsets are less prominent.

In one embodiment, a flow sensor includes a flow channel block defining a flow channel, a molded core tube positioned within the flow channel, a substrate, a bonding element, and a sensor element or chip. The bonding element can be configured to comprise one or more front wire bonds (FWBs) and/or through-the-wafer (TTW) contacts.

As used herein, the term "tube" means a conduit or channel of any shape through which a fluid flows. The cross section of the tube can be cylindrical, polygonal, elliptical, etc. The molded core tube can be formed from a polymeric material, such as Teflon®, or other materials, such as glass, quartz, sapphire and/or metal, such as, for example, stainless steel. The tube can be made of a mixture of different plastics or polymers. The molded core tube generally comprises a wall thickness that removes a surface of the sensor chip from direct contact with a fluid flowing through the molded core tube by a distance corresponding to the wall thickness, thereby desensitizing the sensor to fluid flow variations. Additionally, this tube wall thickness in contact with the sensor chip combines a high dielectric strength and chemical inertness with properties such as hydrophobic, hydrophilic and lipophilic as needed. Such properties may be realized with inorganic or organic materials. Note that as utilized herein the term fluid can be meant generally to refer to a gas or liquid. Thus, sensor packages disclosed herein can be utilized to measure the quality or property of a gas or a liquid.

The film can be enlarged to comprise a potting or molding compound associated with the bonding elements, whereby the molded core tube generally shapes the potting compound. The film itself may be formed from a material such as, for example, an epoxy material. Also, the molded core flow channel can be configured to include a constriction in a cross section of the molded core tube at the sensor chip to optimize performance thereof. The molded core flow channel and the substrate can be replaced by a flat film, which can be wrapped or shrunk about a header and sealed by an O-ring to provide sensor capabilities thereof. The flow tube is generally configured from a flow channel block and can be a disposable flow tube. Additionally, the sensor can be associated and/or integrated with a heat sink mechanism for heat sinking a reference resistance and/or temperature sensor associated with above flow sensor so that the flow sensor does not increase in temperature and drive an associated heater temperature to a point where a fluid flowing through the flow channel boils.

The sensor features a flat, passivated, top surface overlying the heater and sensor elements to provide appropriate electrical isolation. Further, the die, with its through-the-wafer interconnections, eliminates the need for bonding wires with their attendant problems as discussed above. In order to withstand a wide range of pressure levels and operate in harsh environments, the die structure is configured to be very robust. The die is made up of materials that have very low thermal conductivity, thus eliminating the possibility of undesired thermal signal shorts. For example, the die can be fabricated using various glass materials, alumina, or combinations of such materials.

The ability to perform high mass flux sensing operations is largely dependent upon the physical characteristics of the sensor. Most importantly, low thermal conductivity of the die substrate is necessary in order to create a sensor capable of operating in these high mass flux sensing situations. By minimizing the thermal conductivity, interference with sensor heating/cooling effects will be minimized and the sensing capabilities are enhanced. Specifically, the characteristics of the die substrate materials will control the proper route of heat transfer, avoiding transfer through the die substrate from the heater to the sensors. Various materials can provide this characteristic. Historically, silicon nitride of a microbridge sensor chip has been used to provide certain levels of thermal conductivity, while also being easily manufactured. However, its fragility prevents its use in harsh environments.

A more optimum material that exhibits the desired characteristic is glass. Glass, however, has not been previously used because it has not been easily micromachined. That is, it is difficult to form the required structures using glass. Another potential substrate material is alumina, which is widely used for electronics packaging and can be machined to serve as substrate with some desirable characteristics. One undesirable feature, however, is its high thermal conductivity, which would severely reduce the sensitivity of the sensor chip.

Recent developments in glass materials, including photosensitive glass and Pyrex®, have shown that micromachining is possible and extremely effective. Consequently, this material can now provide an alternate die substrate for a micromachined flow and property sensor. The present invention exploits the characteristics of glass (photosensitive glass, fused silica, etc.) or alumina materials to produce a flow and property sensor with optimized physical characteristics. Providing a glass based sensor in a microbrick structure or microfill structure consequently enables the fabrication of a rugged sensor for sensing liquid properties or high mass flux fluid flow, without pressure-stress-induced error signals.

Due to the recent developments in glass, the use of this material as a die substrate generally reduces the amount of structural machining necessary. More specifically, the substrate can now be fabricated in a microbrick structure or microfill structure, which has a substantially solid structure. In this type of sensor die, the heating and sensing elements are placed directly on the substrate and no further processing or structuring is required beneath those elements. Consequently, the substrate itself is continuous beneath the sensing elements creating a more robust sensor die. The characteristics of the glass substrate material allow this microbrick structure to be effectively used in harsh environments.

Flow sensors are either non-isolated, in which the fluid flows directly over the sensing element, or isolated, in which the fluid flow is separated from the sensing element. FIG. 1 illustrates a prior art cross-sectional view 100 of a plastic non-isolated flow channel block 104. FIG. 1 further illustrates a sensor chip 106 which is fastened or in communication with a substrate 102. The substrate 102 can support electrical I/O lead-outs, which may in turn be connected or bonded to various elements on chip 106 via "front wire bonds" (FWBs) 107 or "through-the-wafer" (TTW) contacts (not shown). A top flow channel 111 with an appropriate opening for the chip can then be fastened over the sensing chip 106. Ideally, care should be exercised so as not to spill excess adhesive into the path intended for the fluid. Thus, view 100 represents a drawing of a microsensor, prior to the introduction of the "core mold" concept of the present invention, as explained in further detail herein.

Figure 2:
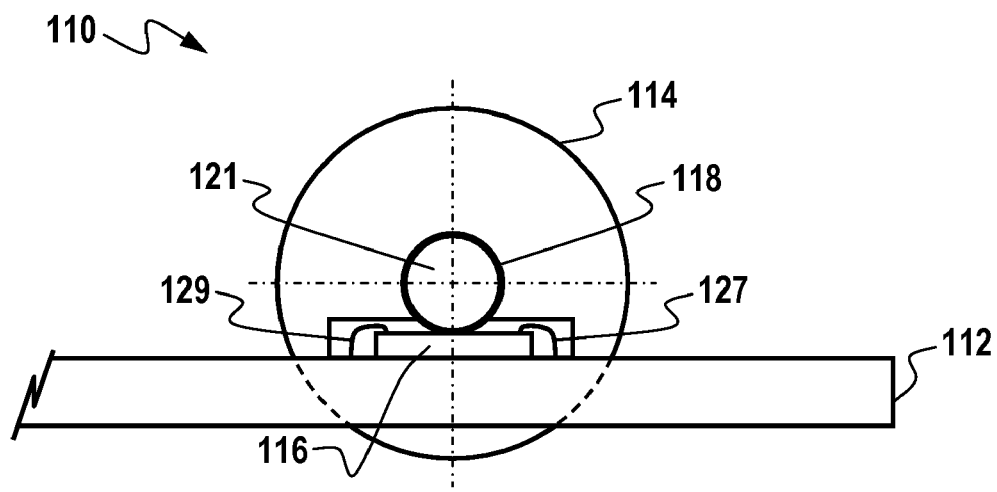
FIG. 2 depicts a cross sectional view of an isolated flow channel block with an inserted core tube.

FIG. 2 depicts a cross sectional view 110 of an isolated flow channel block 104 with an inserted core tube 118. FIG. 2 additionally illustrates a sensor chip 116 and a substrate 112. Flow channel block 114, which is analogous to flow channel block 104 of FIG. 1, now possesses an inserted core tube 118. Substrate 112 may be composed of, for example, alumina, PCB, glass, quartz, or other substrate-type materials. Substrate 112 of FIG. 2 is generally analogous to substrate 102 of FIG. 1. Note that the term "substrate" as utilized herein can refer to a "substrate" or a "substrate board." The composition of the substrate is discussed further below. The flow channel block 114 is also generally analogous to flow channel block 104, with the exception that core tube 118 has been added to block 114. This facilitates the process of fastening flow channel block 114 to an "alumina" substrate 112.

The inserted core tube 118 is not pulled out but is maintained in place to provide the above-discussed advantages. Note that the wall thickness of inserted core tube 118 removes the surface of sensing chip 116 from direct contact with the fluid by a distance corresponding to that thickness, thus desensitizing the sensor to flow changes, which is the price paid for the other benefits mentioned above. Additionally, it is important to note that flow channel block 114 may be configured in the shape of a tube, thereby functioning as a flow tube. Flow channel block 114 thus may form a flow tube.

It can be appreciated by those skilled in the art, however, that flow channel block 114 may be configured in the form of other shapes, such as for example, a triangular-, square-, rectangular-shaped flow channel block, half-circles, or various other geometric shapes. Thus, the shape of flow channel block 114 can be an arbitrary design choice and is not considered a limiting feature of the present invention. Additionally, it can be appreciated that flow channel block 114 can be formed from a variety of materials, including, but not necessarily only, plastic.

In one embodiment, flow channel block 114 is a polymer alignment layer defining a location channel into which core tube 118 is inserted. The alignment layer provides a location channel precisely aligned over sensor chip 116 and allows core tube 118 to be precisely aligned over the sensor chip 116. The composition of an alignment layer is discussed further below.

Substrate 112 can support electrical I/O lead-outs, which may in turn be connected to various elements on sensor chip 116 via "front wire bonds" (FWBs) 127 and 129 illustrated in FIG. 2. Similarly, FWBs 107 and 109 are depicted in FIG. 1. Additionally, bonding elements can be configured as through-the-wafer (TTW) contacts, which are not illustrated in FIGS. 1 and 2. Flow channel block 114 can then be fastened over sensing chip 116 and substrate 112. Ideally, care should be exercised so as not to spill excess adhesive into the path intended for the fluid in FIG. 1. In FIG. 2, core tube 118 can prevent such spills and generally surrounds channel 121 through which a fluid may flow. Note that if core tube 118 is removed from flow channel block 114, channel 121 can be left in place after core tube 118 is removed from molding surrounding core tube 118. In this sense, core tube 118 may also be referred to as a "molded core tube."

The use of such a core tube can thus reduce flow noise, sensitivity, and the risk of contamination of super-clean fluids, fluid leakage, chip corrosion and leakage potential, while improving electrical insulation, structural integrity and thermal measurements thereof derived from an associated sensor chip (e.g., sensor chip 116). Such a core tube can also be used to shape and mold an inner flow channel, which can be removed after curing of the molding compound. The flow sensor can then regain flow sensitivity and maintain low "flow noise" but may lose some chip corrosion protection, fluid and electrical leakage prevention, fluid contamination, non-intrusiveness and structural integrity.

Again, referencing FIG. 2, the substrate 112 can be comprised of alumina, mullite, quartz, or other known materials having coefficient of thermal expansion (CTE) suitably matched to the microsensor die. Silicon is often considered a very effective microsensor body material because it can be easily machined/processed using several well-known silicon processing techniques. In certain applications, such as very high mass flux fluid flow sensing and high-pressure applications, such silicon supported structures as microridges or micromembranes do have certain disadvantages however. Specifically, the thermal isolation characteristics of silicon would limit structural and operational characteristics of a sensor if built directly on silicon. In order to deal with these thermal characteristics, the microsensor body of a silicon-based sensor is configured in a micromembrane type structure, so as to limit the thermal mass below the heater and sensing elements. Obviously, this limits the physical strength of a silicon-based sensor. In addition, this micromembrane configuration is not suitable for high mass flux sensing because its output signal saturates before reacting high flux levels.

In order to effectively operate in harsh environments, the flow sensor must be structurally robust. What is needed is a sensor robust enough to withstand high pressures due to sources (such as high pressure pulses, ultrasonic cleaning, and water hammer). In order to sense high mass flux flow rates, it is also important to have a substrate material with an appropriately low thermal conductivity ($\leq 1.5$ W/(mK)). Certain glass materials provide better thermal isolation characteristics (than silicon), thus increasing the sensing capabilities of the above-outlined micromachined flow and property sensor. The use of glass also allows for a more robust physical structure to be used. These various characteristics result in a more versatile sensor, which can be used in multiple applications. Furthermore, as outlined below, certain techniques provide for effective micromachining of glass based substrates.

The use of glass as a microsensor body material provides multiple features that enhance the capabilities of the sensor. These features include: (1) the automatic electrical insulation for through-the-wafer contacts, (2) lower thermal conductivity than silicon, (3) environmental ruggedness needed to withstand pressure pulses as for sensing liquids, and (4) the ability to use a structurally robust sensor body configuration. Furthermore, the glass-based sensor meets all requirements for chemical inertness, corrosion resistance, and biocompatibility.

As mentioned above, glass provides inherent electrical isolation between various contacts. This is compared with a silicon based sensor where electrical isolation is achieved by incorporating silicon dioxide layers on the substrate unless more costly silicon wafers are used that are grown to be slightly insulating. Obviously, this eliminates one layer of material and one necessary processing step. This is particularly beneficial as the step of growing oxide is time consuming and done at fairly high temperatures.

While the sensor of the present invention can be implemented as glass-based sensor, it is understood that other materials having appropriate physical characteristics could also be used. For example, the substrate can be manufactured out of other materials including glass, quartz, silicon, alumina, or ceramic.

Figure 3:
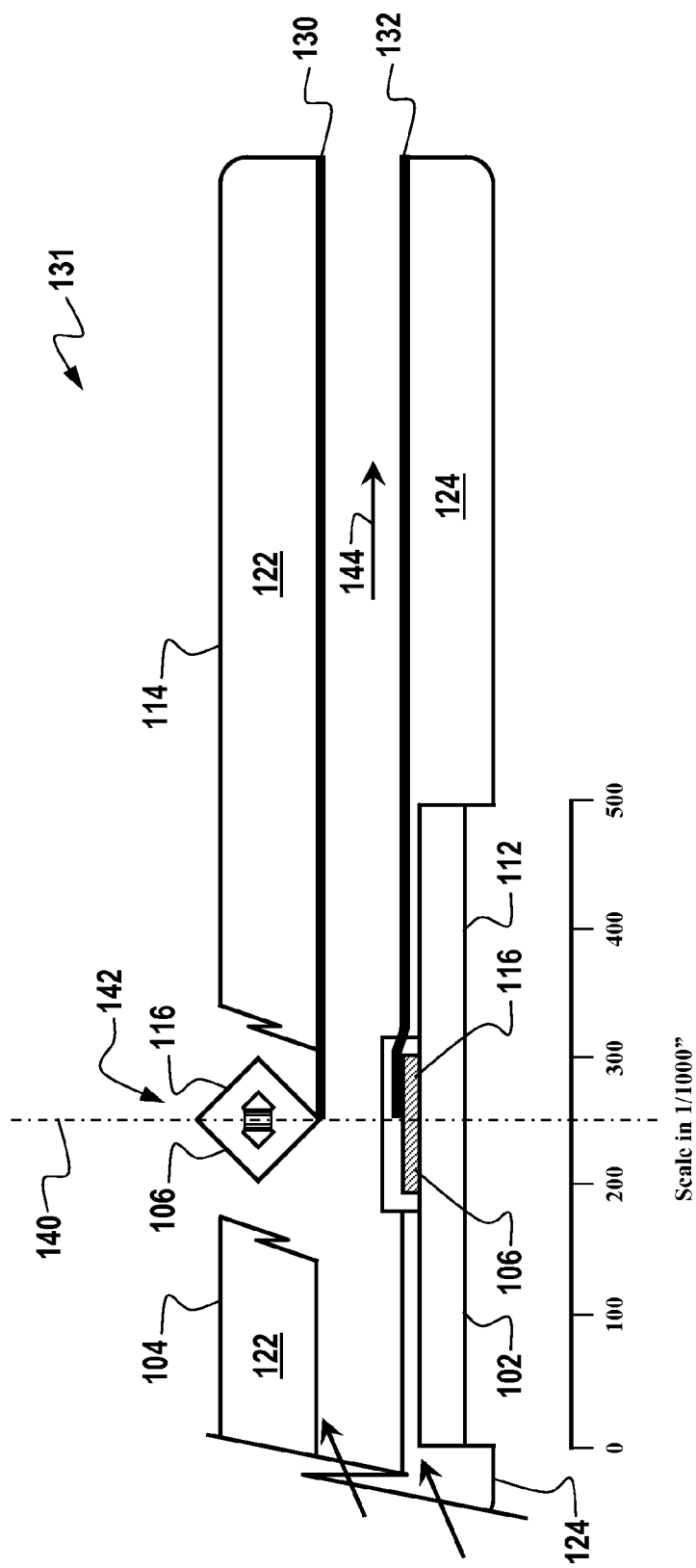
FIG. 3 illustrates a side sectional view of an improved flow channel block with an inserted core.

FIG. 3 illustrates a side cross-sectional view 131 of an improved flow channel block with an inserted core, in accordance with an embodiment of the present invention. The left side of view 131 further illustrates a side-sectional view of the prior art configuration illustrated in FIG. 1, while the right side illustrates the position of the core tube 118. Note that in FIGS. 1 to 3 analogous or like parts are generally indicated by identical reference numerals. For example, flow channel block 104 of FIG. 1 is analogous to flow channel block 114 of FIG. 2. Thus, as indicated in view 131 of FIG. 3, walls 122 and 124 form walls of flow channel blocks 104 and 114.

FIG. 3 is included herein primarily to highlight the differences between the prior art configuration depicted in FIG. 1 and the improved flow channel block design illustrated in FIG. 2. A dashed line 140 in FIG. 3 indicates a separation point between the prior art design of FIG. 1 and the improved design of FIG. 2. Thus, half of sensor chips 106 and 116 are illustrated in FIG. 3, along with half of substrates 102 and 112. A chip top view 142 is also indicated, showing respective halves of sensor chips 106 and 116. As indicated above, walls 122 and 124 form walls of flow channel blocks 104 and 114. Both flow channel blocks 104 and 114 include walls 122 and 124. Walls 122 and 124 are indicated on both sides of dashed line 140. An arrow 144 indicates a flow of fluid through channel 111 and 121. Walls 130 and 132 of inserted core tube 118 of FIG. 2 are also depicted in FIG. 3.

As explained previously, the wall thickness of the tube removes the sensing chip surface from direct contact with the fluid by a distance corresponding to that thickness, thus desensitizing the sensor to flow changes. This effect can be minimized and possibly balanced by increasing the temperature of the heater temperature above an ambient level, and additionally by designing the wall thickness at the sensor chip contact surface to be as small as possible. Note that even with the use of TTW contacts, the suggested use of a core pipe, whether left in place or not after bonding the "clear plastic" part with the "alumina", reduces flow noise and the risk of leakage or corrosion and enables the application of higher heater temperatures, which also leads to higher sensor temperatures and reduced offsets. Note that as utilized herein, the term "bonding" generally connotes electrical contacting with the wire bonds (e.g., FWB), while the term "fastening" generally connotes mechanical securing elements and techniques thereof.

In prior art devices and systems, companies such as for example, Unit Instruments, Emerson Inc. and others, have marketed mass flow controllers based on thermal flow sensors with macroscopic core tubes of stainless steel for decades. Such devices typically feature the heater and sensing elements in the form of wire windings around the core metal tube. This fabrication approach, however, can result in large, slow-responding and costly sensors and is generally an ineffective solution.

Flow sensors, including the overall structures depicted in FIGS. 2 and 3 can be thus designed, especially as the diameter of the core tube decreases, thereby resulting in more favorable surface-to-volume tube ratios. In the embodiment illustrated in FIG. 2, for example, an approximately 0.061" OD Teflon® tubing (i.e., normally used as wire-insulation) can be threaded through the "clear plastic" flow channel 121 cross-sectionally at the sensor chip 116. Either epoxy or RTV can then be injected via a syringe hole towards the chip area until excess spills out, while the unsealed alumina substrate to flow channel block interface remains under vacuum to minimize trapped air bubbles.

Another fabrication technique can also be implemented, in accordance with an another embodiment of the present invention, in which excess adhesive is generally applied to the individual parts prior to joining, evacuating and thereafter bringing the parts together, while squeezing excess adhesive from the bonding surfaces. After curing of the adhesive, the Teflon® core tube can be easily removed, if desired. Measurement of the electrical resistance between the sensing elements and the introduced conductive aqueous salt solution indicates resistances between an initial $\geq$200 MΩ and subsequently after several days, $\geq$30MΩ, with the Teflon® tube removed. No degradation or electrical leakage may be measured if the tube can be left in place.

Figure 4:
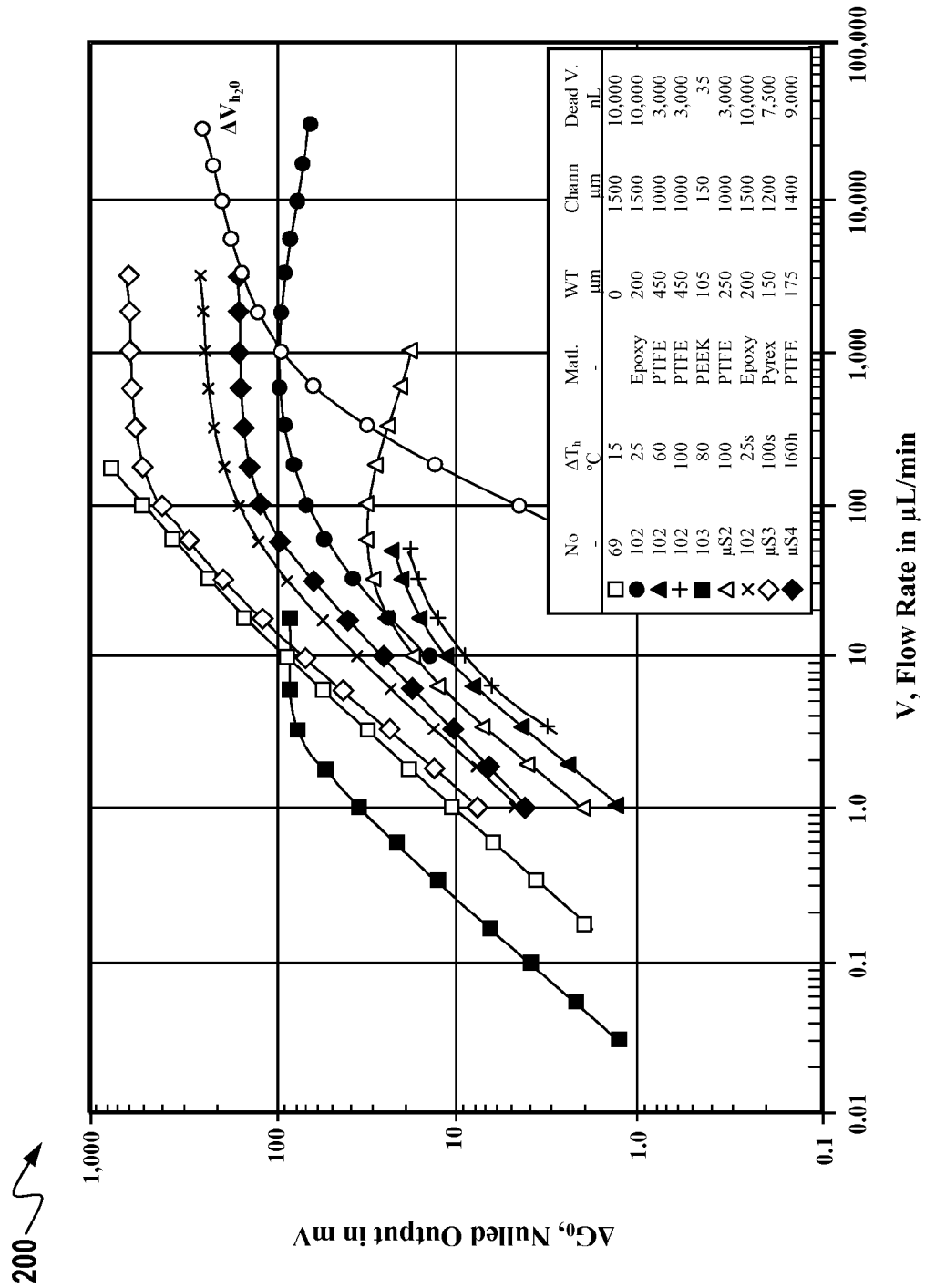
FIG. 4 depicts a graph illustrating the performance of thermal flow sensors with salt water at ambient temperature relative to a flow sensor without a core tube.

FIG. 4 depicts a graph 200 illustrating the performance of flow sensors with salt water at ambient temperature, in accordance with an embodiment of the present invention. FIG. 4 is presented for illustrative and edification purposes only and is thus not considered a limiting feature of the present invention. Graph 200 indicates that measured flow sensor output versus flow for several flow channel configurations and heater temperature values can be obtained. As illustrated in graph 200, flows that occur below 0.5 nL/s are measurable for a smaller core tube of only 150 μm internal diameter. In such instances, noise levels may be approximately in the 1 mV range, for which no compensation for fluctuations in ambient temperatures may be in place. Those skilled in the art can thus appreciate that graph 200 illustrates a range of data collected over time regarding nulled-output versus flow rate. Graph 200 thus generally illustrates the beneficial influence of lower wall thickness (WT) and higher thermal conductivity materials for the core tube, which increases sensitivity and flow ranges. An example of a higher thermal conductivity material, which may be utilized in association with an embodiment of the present invention, is Pyrex®. (Note that Pyrex® is a registered trademark of the Corning Glass Works Corporation of Corning, N.Y. 14831.) A further explanation of FIG. 4 is thus not necessary.

Figure 5:
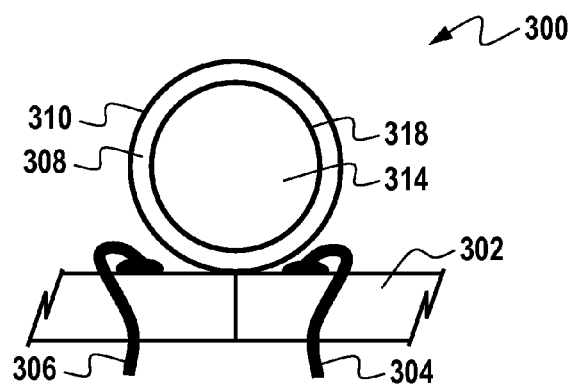
FIG. 5 illustrates a front view of a flow sensor in accordance with an embodiment of the present invention.

FIG. 5 illustrates a front view of a flow sensor 300 that can be implemented in accordance with another embodiment of the present invention. Flow sensor 300 includes an outer surface 310 and an inner surface 312 of a core tube 308 located above a sensing chip 302 with FWBs 306 and 304.

Figure 6:
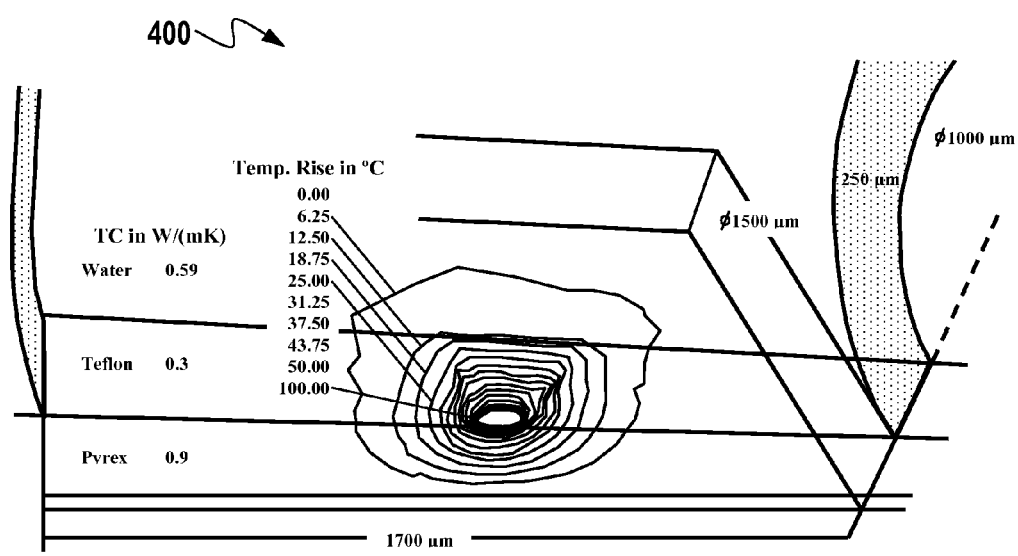
FIG. 6 depicts a cross-sectional perspective view of a temperature field generated by a flow sensor heater, in accordance with an embodiment of the present invention.

FIG. 6 also depicts a cross-sectional side view of a temperature field 400 generated by a flow sensor heater, in accordance with an embodiment of the present invention, whereby the heater can be raised to an exemplary 100° C. above ambient in a plane just 25 μm off the center with no flow present. FIG. 6 generally illustrates the results of a finite-element computation of the temperature profile of a temperature field near the sensor chip (e.g., sensing chip 302 of FIG. 5 or chip 116 of FIG. 2), thus indicating that even the $\Delta T_h$=6.5° C. isotherm barely penetrates the water and accounts for the loss in sensitivity if the thickness of the flow channel block can be chosen to be as large as, for example, 250 μm. The use of thin-wall tubes, made of materials of higher thermal conductivity (e.g., approximately 1 W/(mK)) has been demonstrated as a valid approach to minimizing the sensitivity loss.

It can be appreciated that modifications to the aforementioned improved sensor configuration (i.e., sensor package) can be made in accordance with the present invention. For example, heat sinking a reference resistance, $R_r$, which is not shown in FIG. 6, to achieve proper control of an associated heater, can be implemented by the skilled when familiar with the SoA. Choosing a thin but strong core tube, made of material with intermediate thermal conductivities is another technique that can be utilized, as described above, in accordance with the apparatus of the present invention. Other variations and alternative embodiments are further described below.

Figure 7:
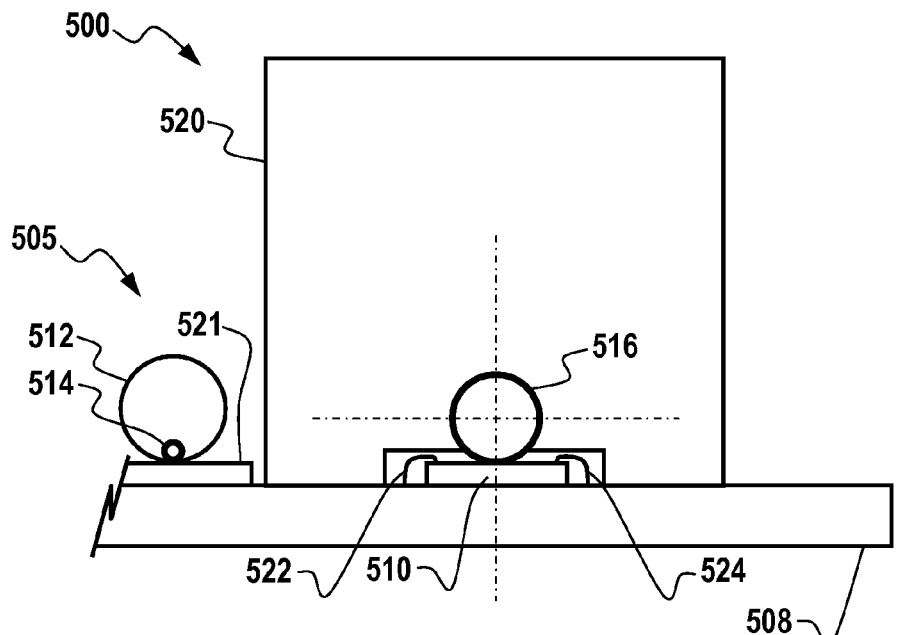
FIG. 7 illustrates a cross-sectional end view of a flow sensor assembly with a glass chip under a Teflon® tube in an epoxy matrix, in accordance with an embodiment of the present invention.

FIG. 7 illustrates a cross-sectional end view 500 of a flow sensor assembly 505 with a glass chip 510 under a Teflon® tube 516 in a flow channel body or block 520 (e.g., of about 0.25×0.25" in cross section), which may be implemented in accordance with a further embodiment of the present invention, and which can be sized to fit into a Honeywell flow channel housing AWM720. As illustrated in FIG. 7, chip 510 can be located above a substrate 508, which may be composed of alumina, glass, or other substrate material. Chip 510 can be configured to include FWB contacts to substrate 508 via wires 522 and 524. Core tube 516 can be 0.060" in diameter. Additionally, a 0.002" wall thickness can be utilized to sense water flows between <10 to >1000 μL/min. The smaller core tube 514 can be inserted into a groove in rod 512, in place of core tube 516 and may be utilized to sense the flows illustrated in FIG. 4 in a range of, for example, 0.03 μL/min to 3 μL/min. Note that rod 512 is positioned generally above block 521 in FIG. 7. Block 521 is in turn positioned above substrate 508.

Figure 8:
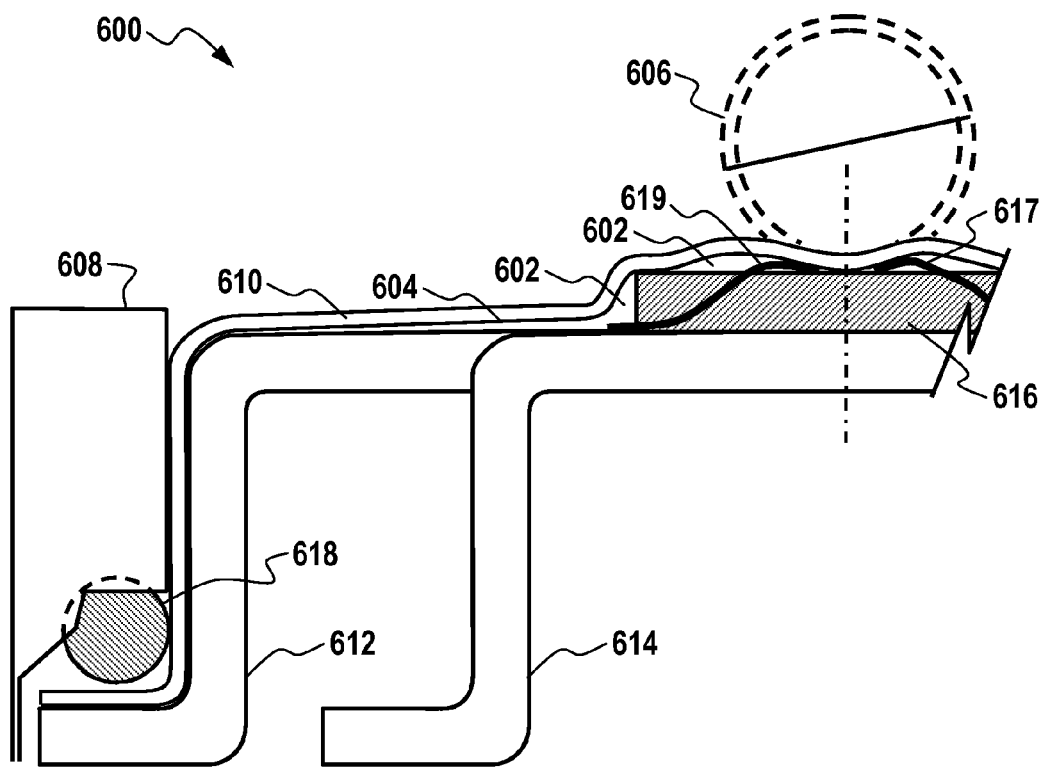
FIG. 8 depicts a graphical diagram illustrating a sensor package for harsh environments applied to large flow channels, or to property measurements, which may be implemented in accordance with an embodiment of the present invention.

FIG. 8 illustrates a sensor package for harsh environments applied to large flow channels, which may be implemented in accordance with an embodiment of the present invention. The sensor chip 616 can be fastened onto a header (e.g., #T08 614 or #T05 612) and electrically bonded to one or more associated posts via wires 617 and 619. Instead of exposing the chip surface to the fluid flowing in a channel as large as 0.5" or more, the sensor chip can be protected by film 610, which may be composed of any number of single or laminated, organic or inorganic materials. The thin film 610 is applied to the sensing element, wherein said thin film is applied thinly, thereby enabling reliable, sensitive, low-noise, non-intrusive, non-contaminating, and flow-channel-disposable measurements thereof. In one embodiment, for example, the thin film is applied to the sensing element at a thickness in an inclusive range from about 0.001-in to about 0.010-in.

Note that a virtual channel 606 is depicted in dashed lines in FIG. 8. Such a virtual channel 606 may be, for example, approximately 0.060-in in diameter. As illustrated in FIG. 8, voids 602 may be filled with adhesive such as epoxy. An underside 604 of the polymer film 610 may be "etched" to promote adhesion. An O-ring 618 can be placed around the base of the header to enable sealing against the fluid in the large channel. The header can be fastened by known fastening techniques against the large flow channel block 608, of which only a corner is illustrated in FIG. 8.

Figure 9:
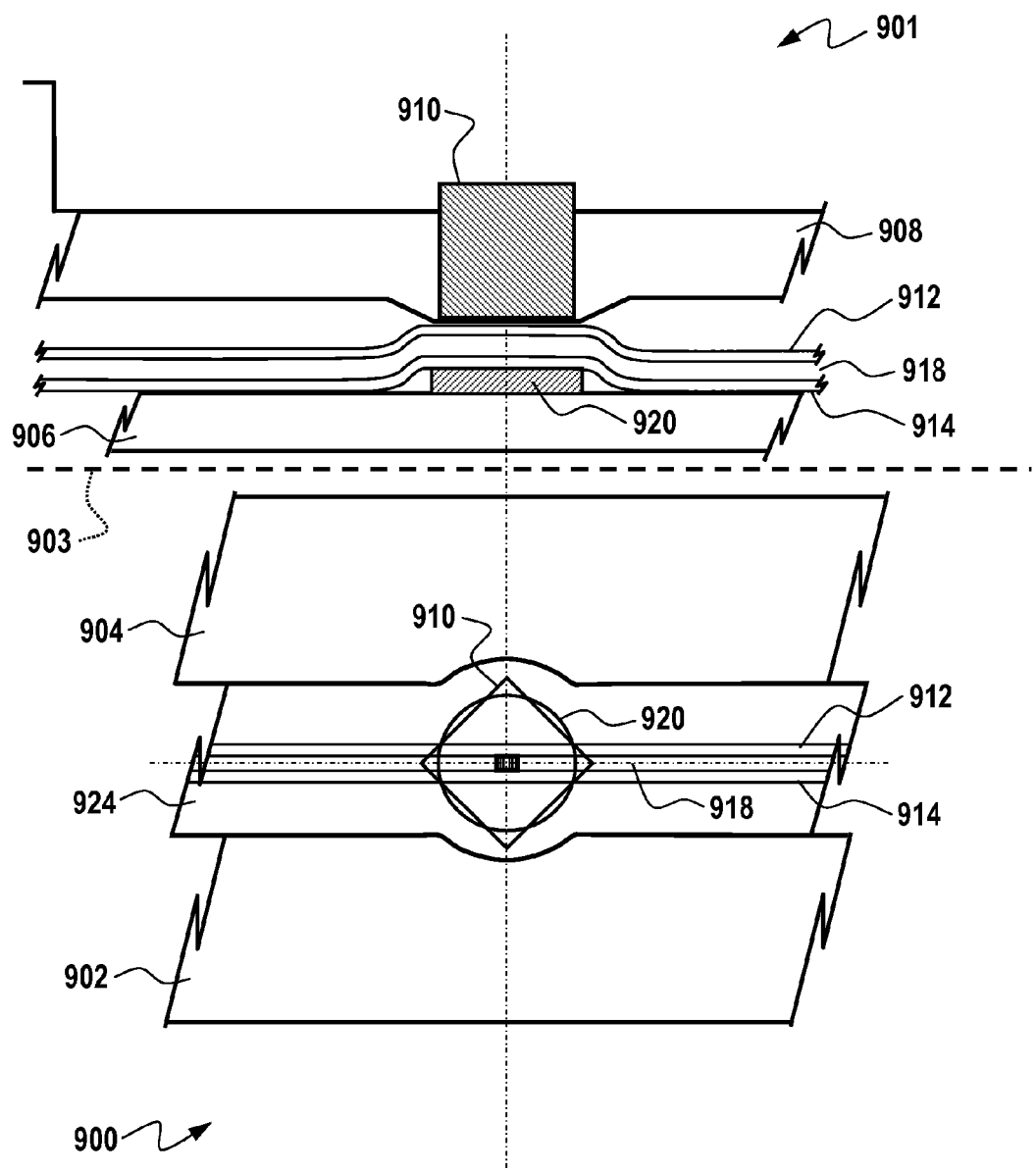
FIG. 9 illustrates a sectional top view and a bottom view of a flow sensor assembly with a small core tube located within walls of a flow channel block thereof, in accordance with an embodiment of the present invention.

FIG. 9 illustrates a sectional top view 901 and a bottom view 900 of a flow sensor assembly with a small core tube 918 (e.g., of ~0.014" outer diameter and 0.006" inner diameter) located within walls 906 and 908 of a flow channel block thereof, in accordance with an embodiment of the present invention. Note that top and bottom views 901 and 900 are separated from one another in FIG. 9 by a dashed line 903. During assembly of the structure illustrated in FIG. 9, an epoxy can be utilized to fill all voids except the inner diameter of core tube 918. Pusher element 910 can be utilized to press core tube walls 912 and 914 onto sensor chip 920 to minimize any void between sensor chip 920 and tube wall 914. This design simplifies for some applications the assembly of small core tubes as explained herein (e.g., the small core tube of FIG. 7). Thus, a simplified yet efficient core tube structure for use with sensor packages for harsh environments can be readily constructed, particularly in view of commercially available parts (e.g., block walls 906, 908, and sensor chip 920, wherein wall 906 can also comprise the circuit bearing substrate).

Figure 10:
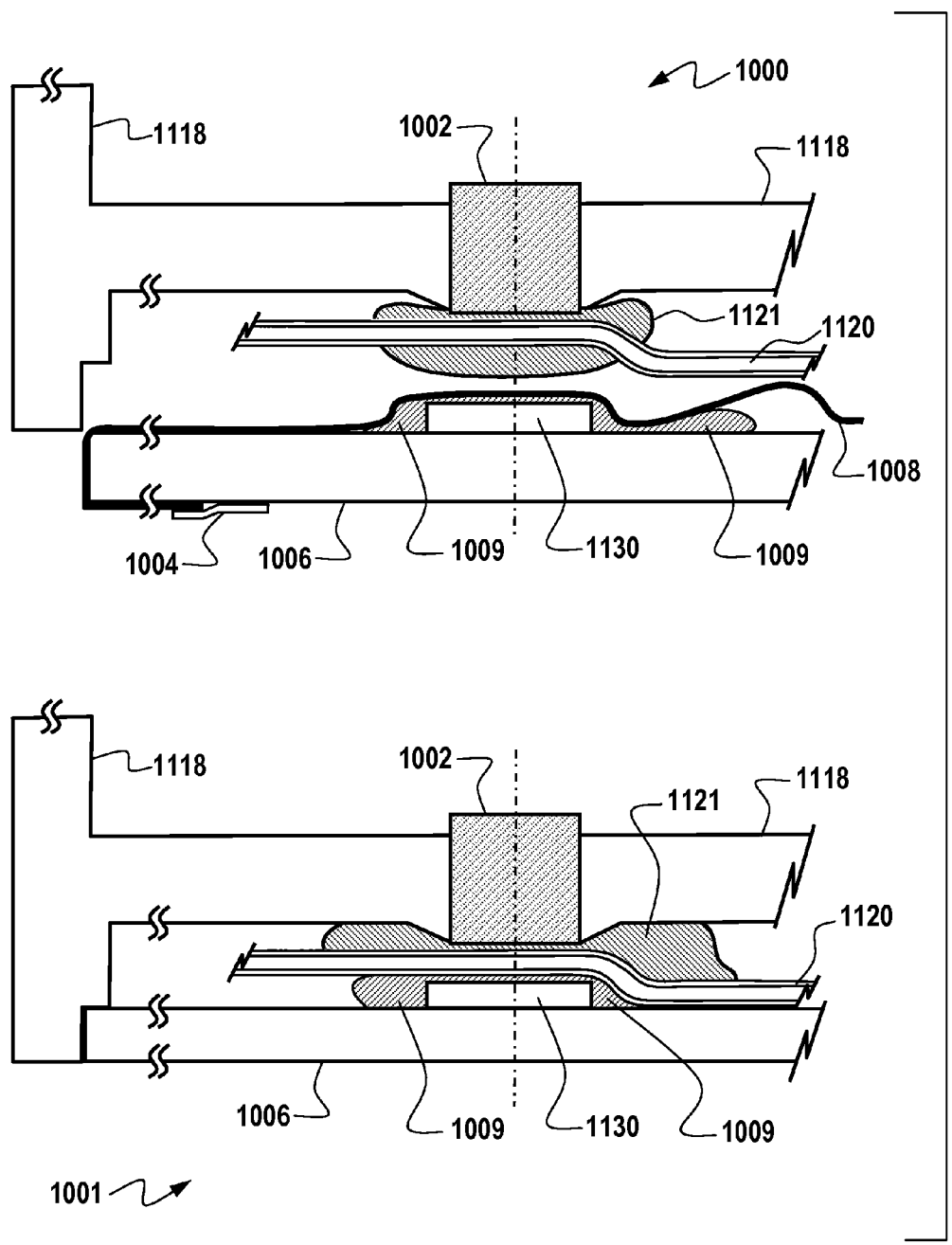
FIG. 10 depicts sectional views of an assembly of a flow channel block and a core tube, in accordance with an embodiment of the present invention.

FIG. 10 depicts sectional views 1000 and 1001 of an assembly of a flow channel block 1119 and a core tube 1120, in accordance with an embodiment of the present invention. View 1000 illustrates an epoxy adhesive 1009 located beneath a film 1008 (e.g., Teflon® tape), which can encase one or more FWBs. During curing and after the insertion of epoxies 1009 and 1121 and assembly thereof, a core tube 1120 can be placed above film 1008 and pressed via a pusher element 1002 onto a sensor chip 1130 and a substrate 1006. Note that pusher element 1002 of FIG. 10 is similar to pusher element 910 of FIG. 9.

By making certain that film 1008 does not adhere to substrate 1006 and sensor chip 1130, nor to epoxy 1121 and flow channel block 1118, one can take the top and bottom halves apart after the epoxy has been cured and remove the film as well. Film 1008 can be formed from a material such as, for example, a Teflon® fluoropolymer or Aclar®. (Note that Aclar® is a registered trademark of the Allied Chemical Corporation of Morris Township, N.J.) The structure indicated in FIG. 10 can thus be fabricated, thereby permitting the perfectly mated top and bottom halves to be reassembled, such that the surface of core tube 1120 contacts the sensing surfaces of sensor chip 1130. After completion of the measurements, the top half of the assembly illustrated in view 1001 of FIG. 10 can be discarded (e.g., it may contain a blood or other biological fluid), without having contaminated the non-disposable and generally more costly part holding the sensor chip 1130 and its calibrated circuit on substrate 1006.

Based on the foregoing it can be appreciated that a number of alternative sensor configurations can be implemented in accordance with the present invention to achieve electrical insulation for liquid or "harsh environment" sensor chips. For example, covering a "to-be-sealed" sensor chip to sense liquid flow or liquid properties with a film that combines high dielectric strength and chemical inertness with hydrophobic properties, whether inorganic or not, may be utilized to achieve such electrical insulation.

Another technique for achieving electrical insulation for liquid or "harsh environment" sensor chips, in accordance with the present invention disclosed herein, involves enlarging and shaping the film as a potting compound of the wire-bonds around the chip, whereby the potting-sealant-adhesive (e.g., epoxy, RTV, etc.) can be shaped by a removable mold core (such as thin tubing or film of fluoropolymer, glass or metal) to reliably provide minimum insulation, while maximizing sensing performance (e.g., higher signal reliability/accuracy due to reduced offsets, lower-noise, longer service life, etc). In such an instance, the tubular mold core tube may be left in place as insulation after potting. The flow sensor itself, according to the present invention disclosed herein, thus can be exposed to the fluid, because the core tube (i.e., core flow tube) can be removed after using it to mold the flow channel. Alternatively, the flow sensor may also be exposed to the fluid if the core tube is left in place. The core tube thus may comprise a disposable flow tube.

In addition, smartly performing the potting enables the fabrication of disposable flow tubes (e.g., for blood or chemical analysis) without disposing of the calibrated sensor and its electronics. Additionally, a constriction in the cross section of the core tube can be provided at the site of the sensor chip (e.g., see FIG. 1) to optimize performance at the location of the highest flow velocity (and signal) and governing pressure drop (i.e., to minimize overall $\Delta p$).

Furthermore, the tube and the flat substrate can be replaced by a flat film (e.g. 20-100 μm thick Teflon®) wrapped or shrunk around a header such as, for example, a TO5 or TO18, and sealed by an O-ring 618 as shown in FIG. 8. Finally, as indicated previously, heat sinking the reference resistance, $R_r$, so that it does not heat up and accidentally drive the heater temperature too high and boil the liquid can be utilized to achieve electrical insulation for liquid or "harsh environment" sensor chips. For example, a small metallic thermal conductor may be utilized, which can be epoxied onto the $R_r$, and increase its heat exchange surface in a direction away from heater resistance, $R_h$. Another aspect of the present invention is related to the alignment of flow channels over a sensor chip. The use of an alignment layer creating a location channel provides another technique for achieving electrical insulation for "harsh environment" sensor chips.

While many different materials may be used to make a fluid flow sensor, the choice of material can drastically affect the sensor's performance. A suitable material for the sensor substrate would have a relatively low thermal conductivity. A low thermal conductivity is important to maintain the sensitivity for the sensor. With a relatively low thermal conductivity, all heating/cooling effects presented to the various sensing elements are caused predominantly by the fluid to be sensed. Stated alternatively, it is important to ensure that heat is not transmitted through the substrate excessively, resulting in signal shorts.

In addition to the above referenced thermal characteristics, it is highly desirable for the overall flow sensor to be chemically inert, corrosion resistant, highly temperature stable, electrically isolated, and biocompatible. The sensor features a flat top surface overlying the heater and sensor elements to provide appropriate electrical isolation. The top surface of the sensor can be passivated. The heater and sensor elements are embedded in or attached to a substrate, or die. The sensor can be configured to include one or more front wire bonds and/or through-the-wafer contacts. Through-the-wafer interconnections eliminate the need for bonding wires. The substrate is made up of materials chosen to have a relatively low thermal conductivity, thus eliminating the possibility of undesired thermal signal shorts. For example, the substrate may be fabricated using various glass materials, silicon, alumina, quartz, ceramic, polymers, metal, or combinations of such materials.

As shown in FIGS. 11A and 11B, the sensor 2010 includes substrate 2020, sensing element 2070, guide elements 2030 formed in an alignment layer, a flow channel 2040 defined by the guide elements 2030, and molded element 2050 defining flow channel extensions 2080, 2081. Substrate 2020 has notches 2060 cut into the top surface to accommodate the molded element 2050. Flow channel 2040 is aligned over sensing element 2070, which includes a heater 2090 and thermal sensors 20100, 20101. The substrate 2020 can be any conventional material used for microsensors, including silicon, ceramic, metal, glass, such as Pyrex®, or quartz.

The fluid flow path, indicated by the arrow in FIG. 11B, is precisely aligned over the sensing element 2070 in the sensor 2010 shown in FIGS. 11A and 11B through the use of guide elements 2031 defining flow channel 2040. The alignment layer is a polymer material deposited over an entire wafer containing multiple sensing elements 2070 arranged in a pattern. In one embodiment, the polymer is a positive resist such as poly(methyl methacrylate) (PMMA). In another embodiment, the polymer is an epoxy based negative resist. One such resist is SU-8, which is sensitive to UV radiation, and is thermally and chemically stable after development. The alignment layer is masked, and guide elements 2030 are formed by photolithography.

Figure 13:
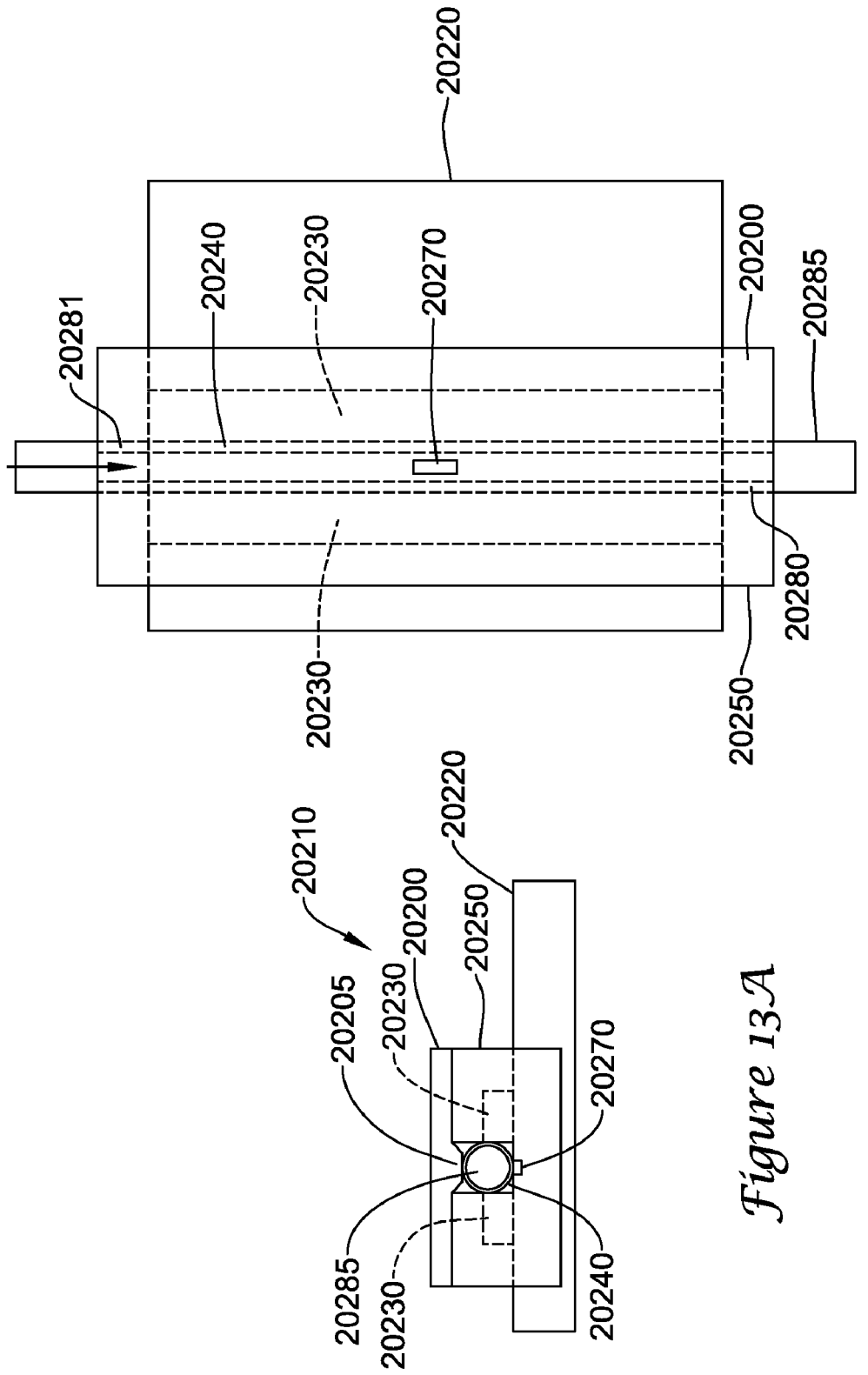
FIGS. 13A and 13B are front and top views, respectively, of a further embodiment of microsensor according to the invention.
Figure 15:
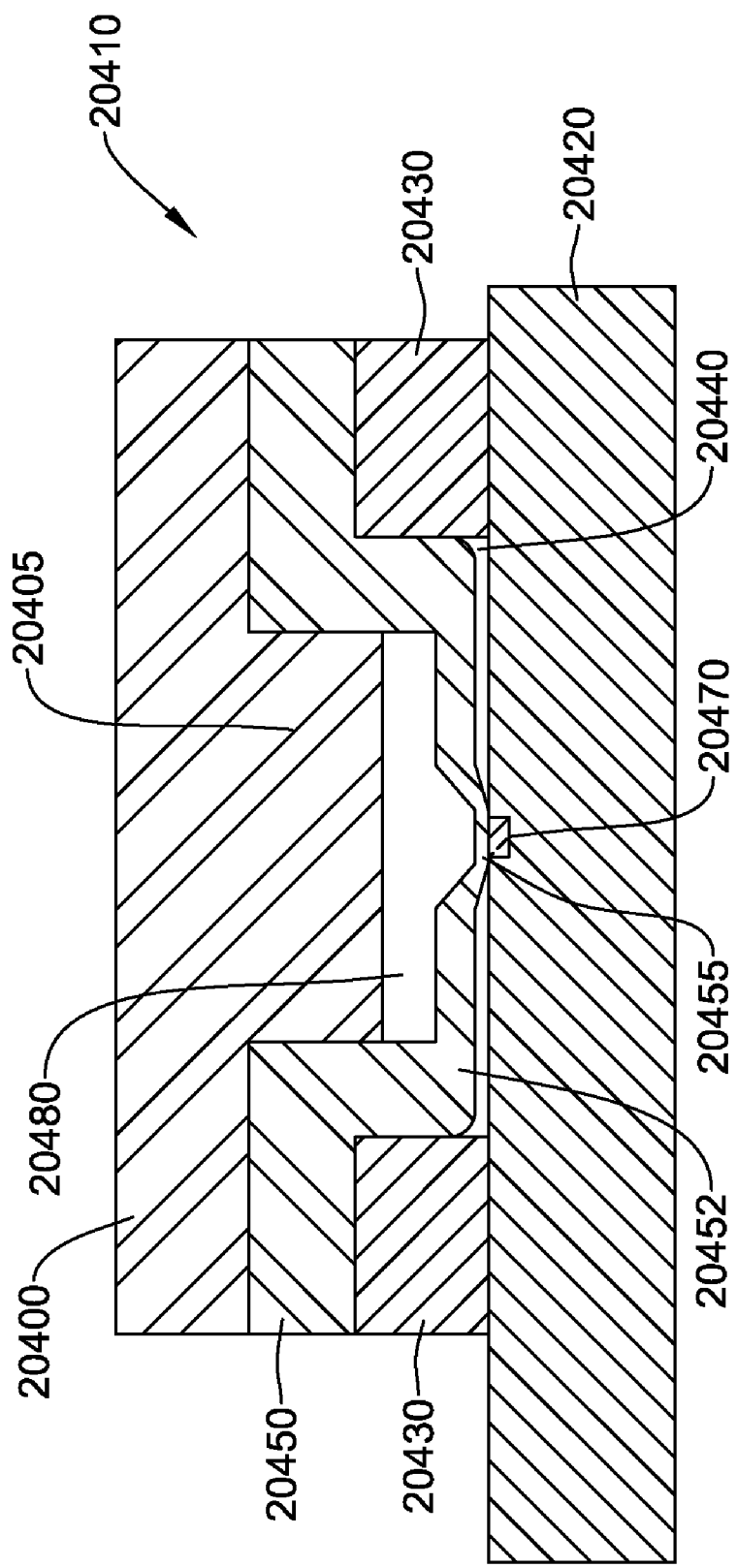
Figure 16:
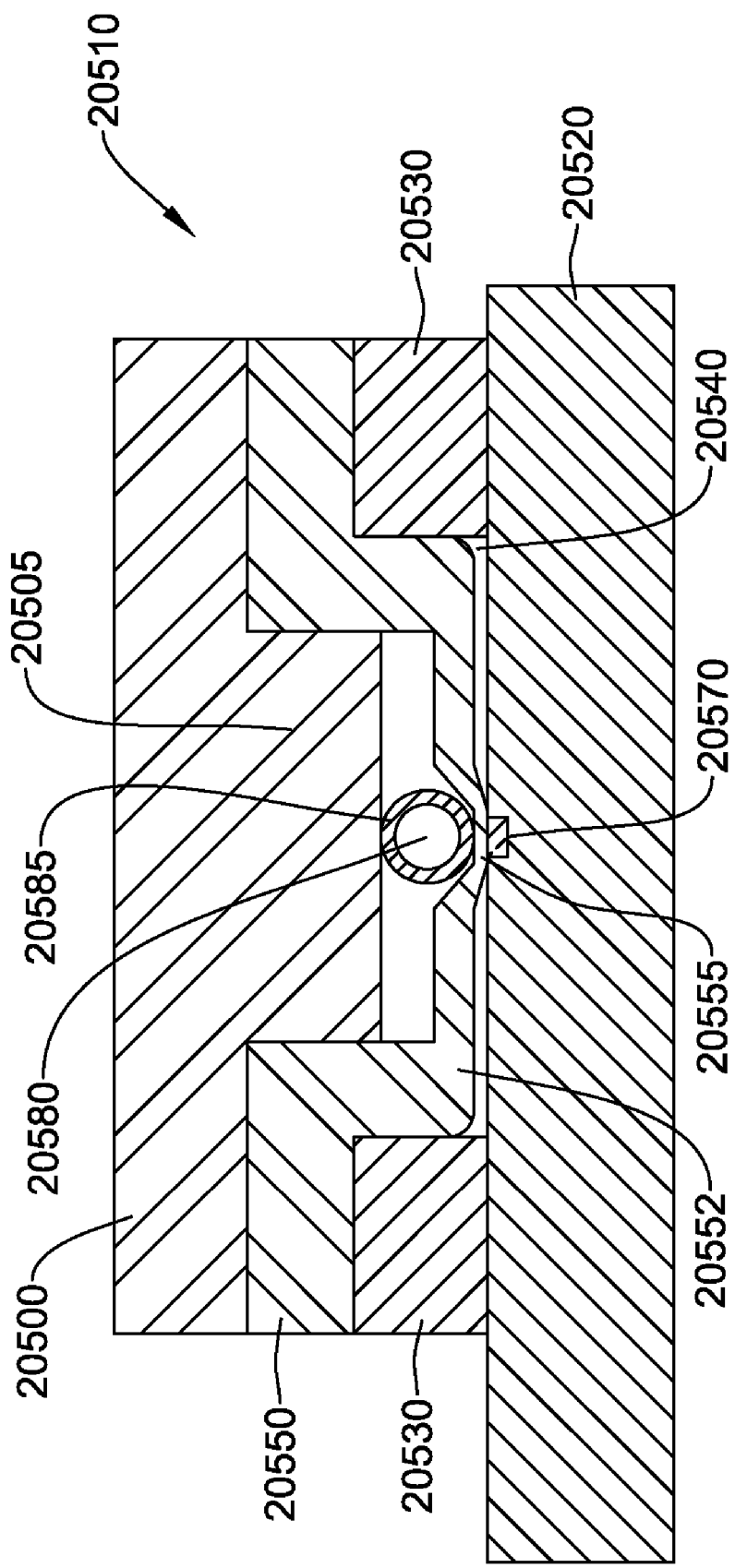

The guide elements 2030 are positioned adjacent the sensing elements and serve to guide or align a flow channel over each sensing element. In one embodiment, shown in FIG. 17, a single guide element 20630 is positioned adjacent the sensing element 20670, and a molded element 20650 having a flow channel 20680 is positioned over the guide element 20630 to align the flow channel 20680 over the sensing element 20670. In other embodiments, the alignment layer is masked such that the guide elements create channels with vertical walls aligned over the sensing elements. In one embodiment, shown in FIGS. 11A and 11B, the alignment layer is masked to create guide elements 2030 on either side of the sensing element 2070. In this embodiment, the guide elements 2030 form a flow channel 2040 that serves as the flow path. In other embodiments, shown in FIGS. 13-16, the guide elements form a location channel 20240, 20340, 20440, 20540 into which is placed a flow tube 20285 (FIG. 13A), molded element 20350, 20450 (FIGS. 14, 15), or both a molded element 20550 and flow tube 20585 (FIG. 16). The flow tube or molded element in these embodiments functions as the flow path.

In another embodiment, the substrate is a silicon wafer and the guide elements are etched using a procedure such as deep reactive ion etching (DRIE). In a further embodiment, the guide element is a V-groove formed by an anisotropic etch of KOH and water. A truncated V-groove having a flat bottom of etch resistant boron doped silicon formed initially beneath a layer of epitaxially grown silicon can also be used.

Forming the guide elements precisely aligned adjacent to the sensing elements while processing is still at the wafer level allows for multiple sensors to be manufactured with identically aligned flow paths. The wafer is diced into individual sensors, and molded elements or flow tubes can be positioned over the guide elements to provide a fluid flow channel precisely aligned over the sensing element.

In the sensor shown in FIGS. 11A and 11B, guide elements 2030 define the flow channel 2040, which is also the flow path. The substrate 2020 forms the bottom of the flow path, the guide elements 2030 form the walls of the flow path, and molded element 2050 forms the top of the flow path. Molded element 2050 includes flow channel extensions 2080, 2081 that connect to the ends of the flow channel 2040 to provide an interface with a fluid system. Molded element 2050 can be attached to the substrate 2020 with an adhesive. The guide elements 2030 provide a barrier to prevent migration of the adhesive into the flow path or onto the sensing element. In this embodiment, multiple sensors with identical, precisely aligned flow paths can be produced with minimal post-wafer processing.

Figure 12:
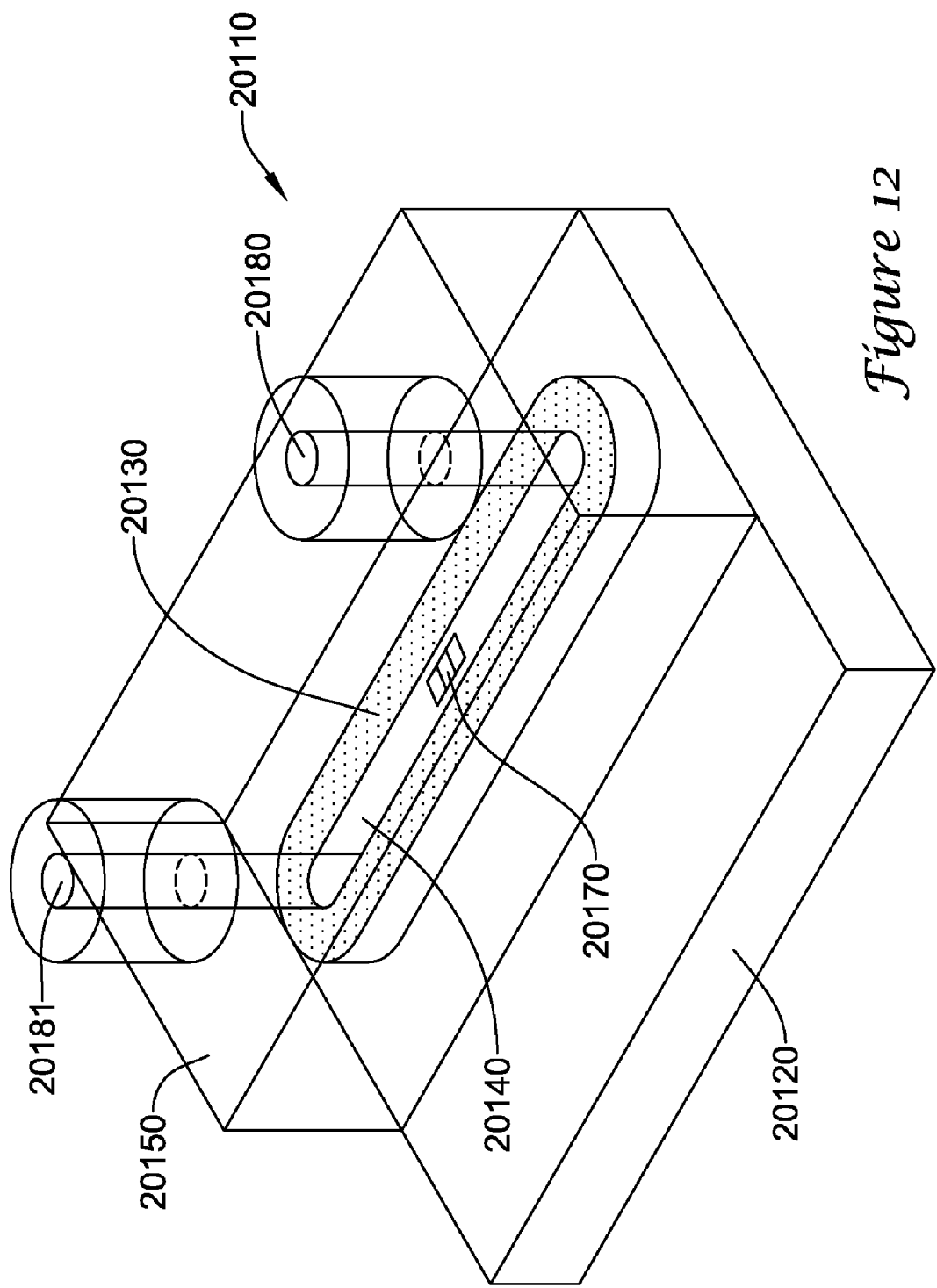
FIG. 12 is a perspective view of another embodiment of microsensor according to the invention.

Another embodiment of sensor is shown in FIG. 12. Substrate 20120 has a sensing element 20170. A single oval guide element 20130 is formed in the alignment layer and defines a flow channel 20140 aligned over sensing element 20170. Molded element 20150 is configured to fit over guide element 20130 and form the top of the flow channel 20140. Molded element 20150 includes flow channel extensions 20180, 20181 that connect with the ends of the flow channel 20140 at an angle and provide an interface with a fluid system. In some embodiments, flow channel extensions 20180, 20181 have the same dimensions. In other embodiments, the two flow channel extensions 20180, 20181 are differently sized. For example, the flow channel extensions may have different inner diameters to accommodate the tubing or flow paths in the larger fluid flow system in which the flow sensor is placed. In sensors having one or more angles in the flow path, the sensing element 20170 is positioned at a distance from the last upstream angle that is greater than or equal to ten times the diameter of the flow channel. This spacing allows turbulence in the fluid caused by the angle to dissipate before the fluid passes over the sensing element.

The flow sensor embodiments shown in FIGS. 11A, 11B, and 12 are non-isolated sensors. The fluid flow path is directly over the sensing element 2070, 20170 and is bound by the substrate 2020, 20120 on the bottom, the guide elements 2030, 20130 on the sides, and the molded element 2050, 20150 on the top. The flow sensors shown in FIGS. 13A, 13B, and 14-16 are isolated sensors.

The flow sensor 20210 shown in FIGS. 13A and 13B includes a substrate 20220, an alignment layer defining guide elements 20230 that form a location channel 20240 over a sensing element 20270, a molded element 20250 including flow channel extensions 20280, 20281, a flow tube 20285, and a cap 20200. The guide elements 20230 are precisely aligned to form the location channel 20240 over the sensing element 20270 and serve to align the molded element 20250 and flow tube 20285 over the sensing element 20270. The molded element 20250 provides additional support for the flow tube 20285. Cap 20200 serves to hold the flow tube 20285 in contact with the sensing element 20270. The flow tube 20285 provides an isolated flow path over the sensing element 20270.

The flow tube 20285 has a wall thickness that removes a surface of the sensor from direct contact with a fluid flowing through the flow tube by a distance corresponding to the wall thickness, thereby desensitizing the sensor to fluid flow variations and protecting the sensor from what may generically be referred to as a "harsh environment." A harsh environment may include fluids that are contaminated, dirty, condensing, corrosive, radioactive, etc. Also included are fluids that may overheat, leave deposits, or freeze up the device. The cross section of the flow tube can be cylindrical, polygonal, elliptical, etc. In some embodiments, the flow tube 20285 is disposable, providing a flow sensor that is reusable for multiple contaminated fluid samples, such as blood. To change the flow tube 20285, the cap 20200 is removed, the used flow tube is replaced with a new flow tube and the cap is replaced. Additionally, this tube wall thickness in contact with the sensor combines a high dielectric strength and chemical inertness with properties such as hydrophobic, hydrophilic and lipophilic as needed. Such properties may be realized with inorganic or organic materials.

In some embodiments, cap 20200 includes a protrusion 20205 sized to extend downward to hold smaller flow tubes 20285 in contact with the sensing element 20270. The sizes of the molded element 20250 and cap 20200 can be selected to provide stability for various sizes of flow tubes 20285. In this way, multiple sensors cut from a single wafer, each with identical sized location channels 20240, can be used with different sizes of flow tubes 20285. Additionally, the molded element 20250 can extend into the location channel 20240 to provide a narrower channel for receiving small diameter flow tubes 20285. The molded element 20250 can be attached to the substrate 20220 and cap 20200 using adhesive. The guide elements 20230 provide a barrier to prevent migration of the adhesive into the flow path or onto the sensing element.

The tube 20285, molded element 20250, and cap 20200 can be made of glass such as Pyrex®, fused silica, quartz, sapphire, ceramic, epoxy, one or more polymers such as PEEK (polyetheretherketone), PTFE (polytetrafluoroethylene), or Teflon®, or metal such as stainless steel. Mixtures of different types of glass or mixtures of different polymers can also be used to manufacture the tube 20285, molded element 20250, and cap 20200. A stainless steel flow tube 20285 can be attached to the device with heat transfer paste or fluid. Oil can be added to the joint between the tube 20285 and molded element 20250 and/or substrate 20220 to enhance heat transfer.

Figure 14:
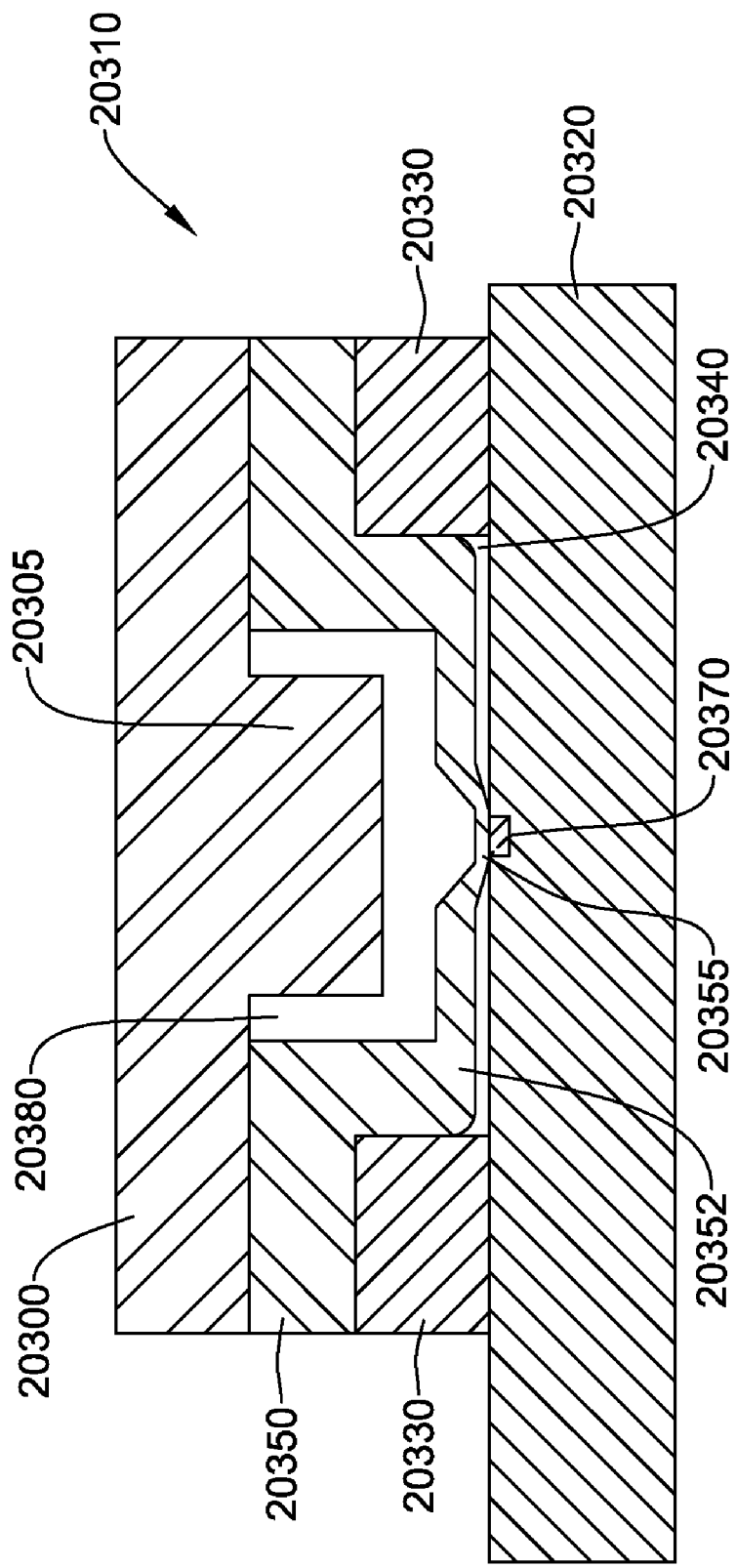
FIGS. 14-17 are front cross-section views of other embodiments of the invention in which guide elements provide alignment for a flow channel or flow tube.

Another embodiment of isolated flow sensor is shown in FIG. 14. The location channel 20340 formed between guide elements 20330 is wider than the sensing element 20370 on the substrate 20320. A molded element 20350 extends over the guide elements 20330 and forms the bottom and sides of a flow channel 20380 that fits within the location channel 20340. A cap 20300 forms the top of the flow channel 20380. In one embodiment, the molded element 20350 has a flow channel bottom 20352 with a thin region 20355 that contacts the sensing element 20370. The remaining flow channel bottom 20352 is spaced apart from the substrate 20320, forming air pockets to reduce loss of the thermal signal. Sensors with different sized flow channels 20380 can be made from the same wafer by using molded elements 20350 with different sized flow channels 20380. In some embodiments, the molded element 20350 is disposable and replaceable. The cap 20300 can also be disposable. Additionally, the cap 20300 can have a protrusion 20305 extending into the flow channel 20380 to alter the dimensions of the flow channel 20380. As shown in FIG. 15, a cap 20400 with a protrusion 20405 extending across the flow channel 20480 reduces the height and overall dimensions of the flow channel 20480. The interface between the exterior of the molded element 20450 and the interior of the location channel 20440 provides accurate and precise alignment of the flow path over the sensing element, regardless of the interior size of flow channel 20480.

In a further embodiment, shown in FIG. 16, a flow tube 20585 is positioned over a thin region 20555 in the flow channel bottom 20552 of molded element 20550. The flow tube 20585 forms the flow channel 20580. The molded element 20550 is aligned over the sensing element 20570 by the guide elements 20530. Cap 20500 contacts the top of the flow tube 20585 and maintains the flow tube 20585 in position. In some embodiments, adhesive is also used to maintain flow tube 20585 in position. In one embodiment, the flow tube 20585 is disposable and replaceable. This embodiment is particularly suited for analyzing fluids that are toxic, corrosive, hazardous, contaminated, etc.

Figure 17:
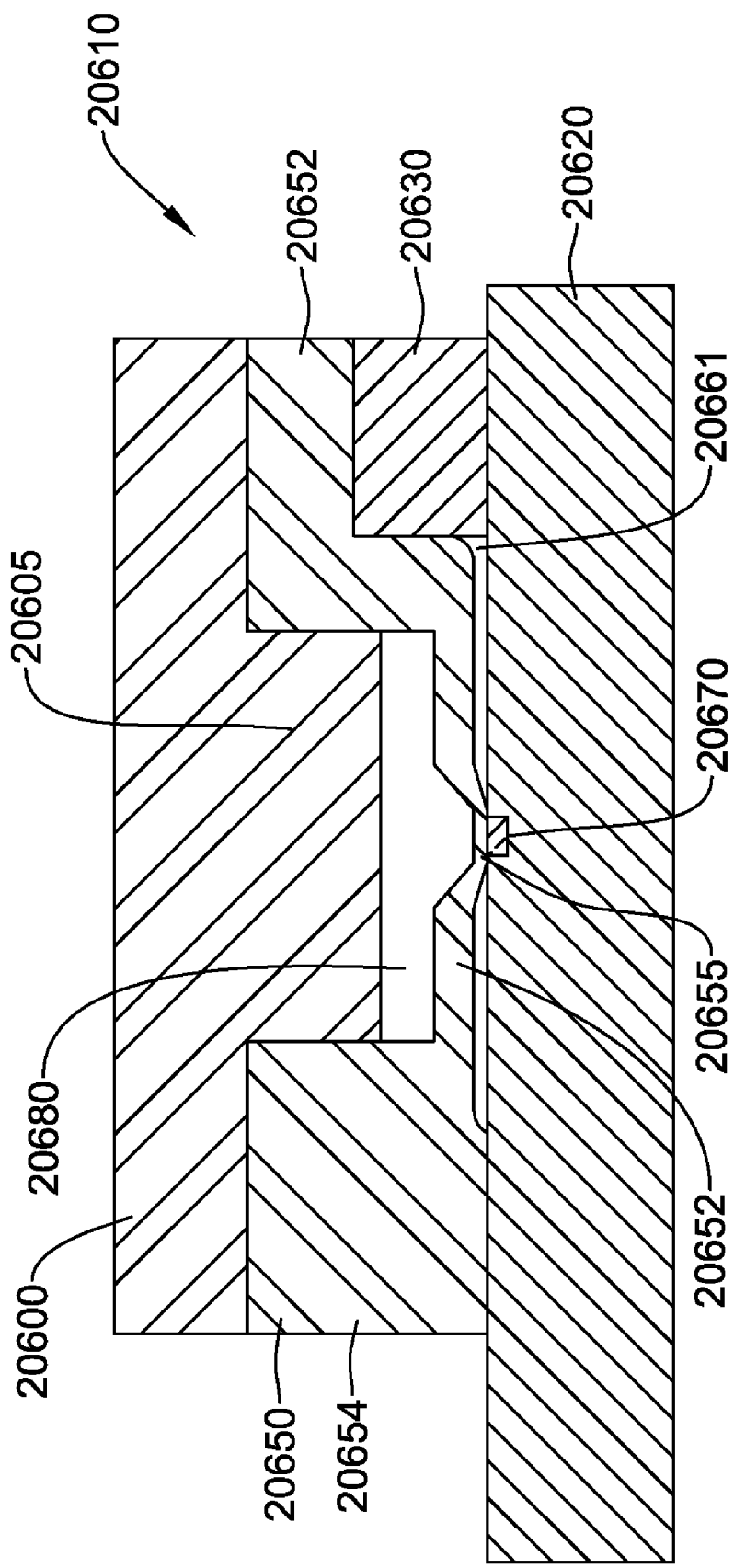

Another embodiment of isolated flow sensor is shown in FIG. 17. An alignment layer is deposited onto a substrate 20620 and a single guide element 20630 is formed in the alignment layer. The guide element 20630 is adjacent the sensing element 20670 on the substrate 20620. A molded element 20650 having a first side 20652 a second side 20654 and a flow channel 20680 therebetween is positioned such that the first side 20652 extends over the guide element 20630 to align the flow channel 20680 over the sensing element 20670. A cap 20600 forms the top of the flow channel 20680. In one embodiment, the molded element 20650 has a flow channel bottom 20652 with a thin region 20655 that contacts the sensing element 20670. In some embodiments, the remaining flow channel bottom 20652 is spaced apart from the substrate 20620, forming air pockets 20661 to reduce loss of the thermal signal.

Figure 18:
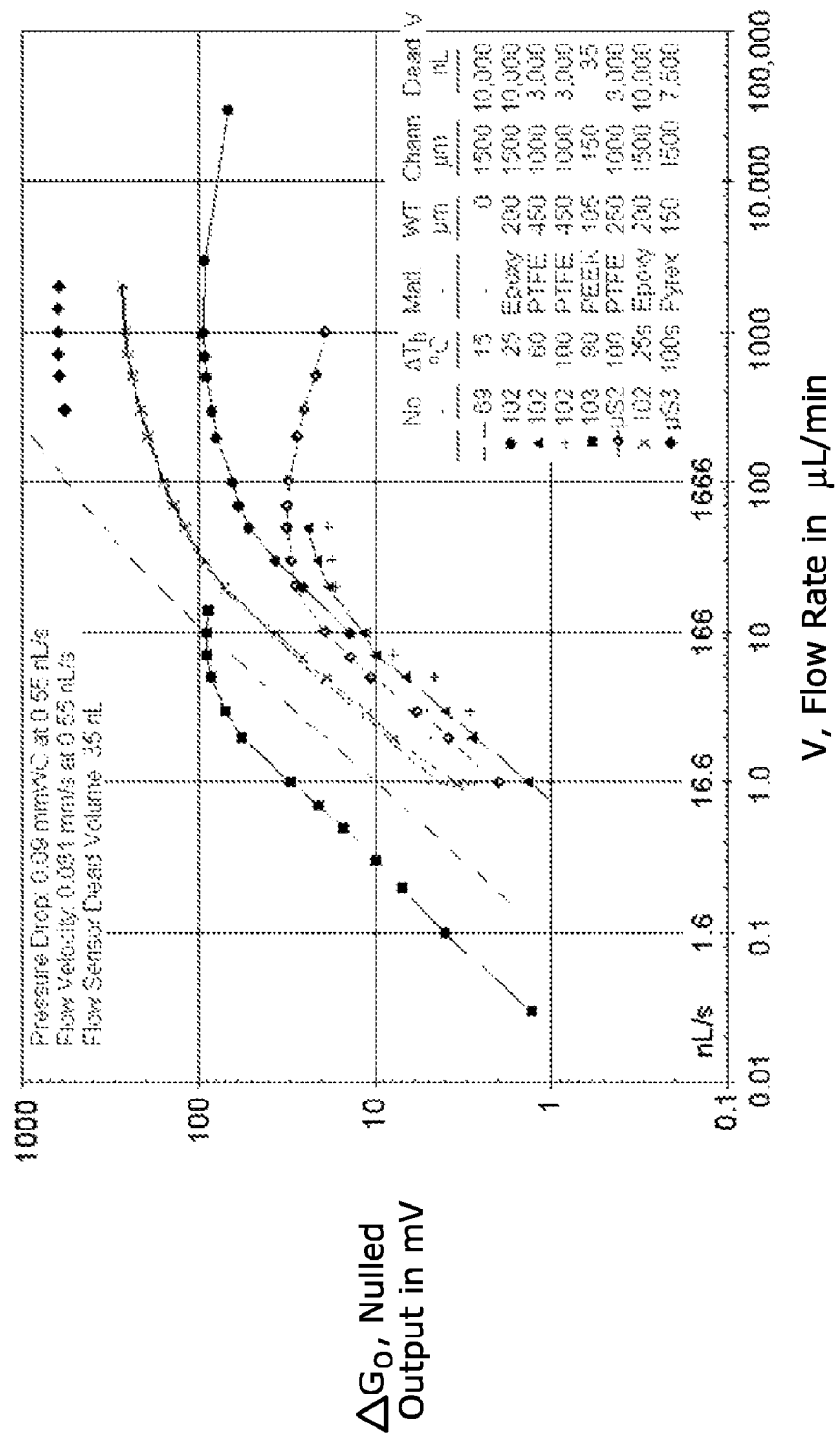
FIG. 18 is a graph illustrating the performance of thermal flow sensors made of different materials and having different wall thicknesses (WT), with salt water at ambient temperature relative to a flow sensor.

FIG. 18 depicts a graph illustrating the performance of flow sensors with salt water at ambient temperature, in accordance with an embodiment of the present invention. FIG. 18 indicates that measured flow sensor output versus flow for several flow channel configurations and heater temperature values can be obtained. As illustrated in the graph, flows that occur below 0.5μL/min are measurable for a smaller core tube of only 150μm internal diameter. In such instances, noise levels may be approximately in the 1mV range, for which no compensation for fluctuations in ambient temperatures may be in place. Those skilled in the art can thus appreciate that the graph illustrates a range of data collected over time regarding nulled-output versus flow rate. FIG. 18 thus generally illustrates the beneficial influence of lower wall thickness (WT) and higher thermal conductivity materials for the core tube, which increases sensitivity and flow ranges. An example of a higher thermal conductivity material, which may be utilized in association with an embodiment of the present invention, is Pyrex®. (Note that Pyrex® is a registered trademark of the Corning Glass Works Corporation of Corning, N.Y. 14831.)

Figure 19:
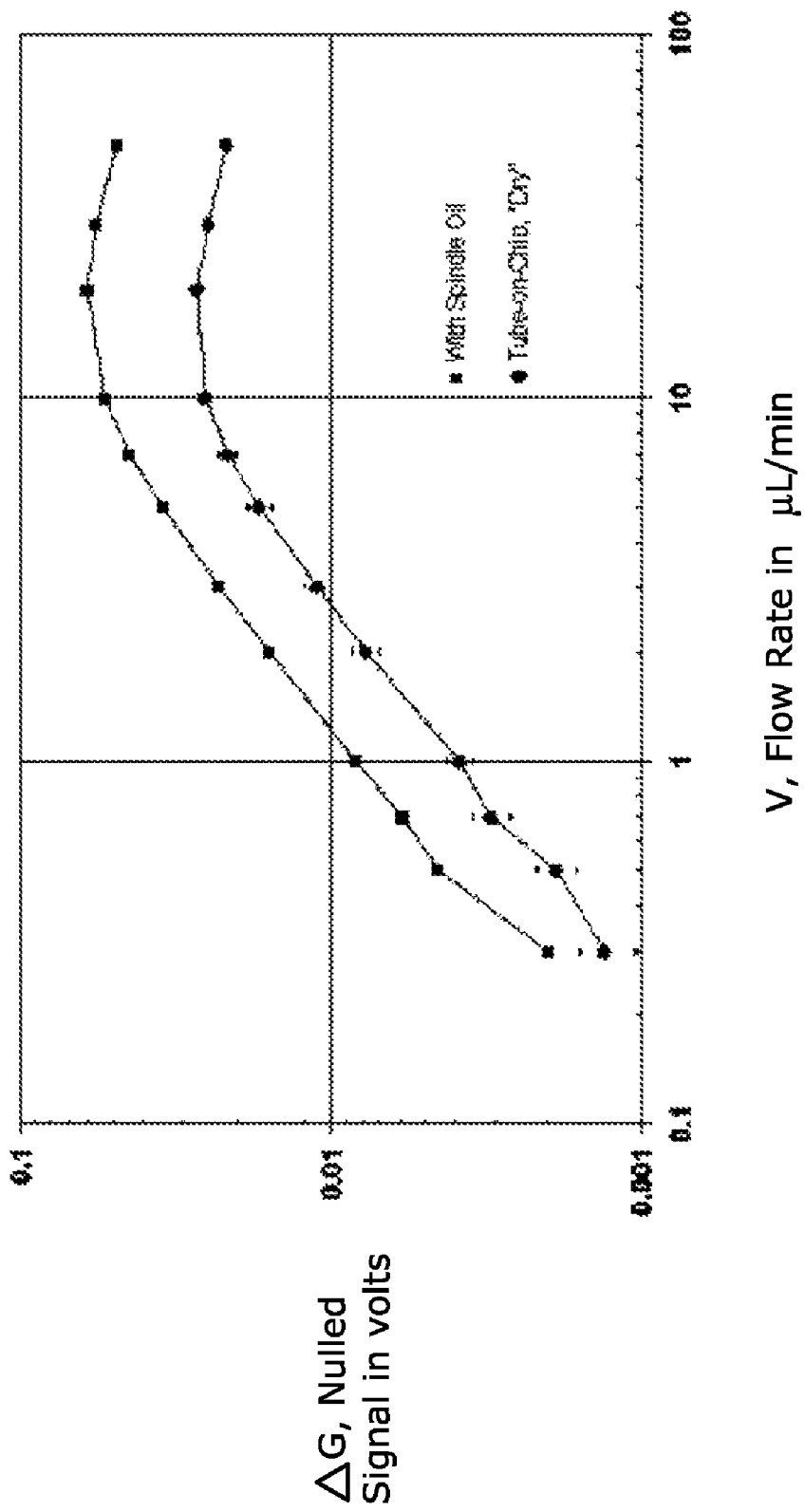
FIG. 19 is a graph illustrating the performance of a stainless steel flow tube with and without oil added to the junction between the flow tube and microbrick.

FIG. 19 depicts a graph illustrating the performance of flow sensors with stainless steel flow tubes on a Pyrex® microbrick with and without oil. The stainless steel flow tube had an inner diameter of 0.004inches and an outer diameter of 0.008inches. Water was used as the fluid. As show in the graph, a drop of oil added to the joint between the flow tube and substrate enhanced heat transfer and increased the signal approximately two-fold.

The flow sensor package disclosed herein offers several advantages over prior art liquid flow sensor packaging approaches. For example, the application of reliably controlling the thickness of the insulating layer, molded element, or flow tube can eliminate electrical leakages and the risk of electrical shorts. This controlled thickness also enables the application of larger voltages to the sensor heating elements, thus higher heater temperatures, and thus leads to larger output signals, reduced effect of sensor and electronic offsets and without boiling the liquid. An isolated flow channel located above the chip cuts down on flow noise while providing the aforementioned benefits, including eliminating the risk of fluid leakage or corrosion and, additionally, providing electrical insulation of the chip contacts. In addition, the isolated flow channel can provide a "clean", contaminant-free environment for preserving the maximum fluid cleanliness.

Thus, according to the invention described herein, a sensor can be configured to generally include a flow path formed over a sensor chip for sensing fluid flow, wherein a fluid in the flow path surrounds the sensor chip. Alternatively, the sensor chip can be isolated from the flow path by a flow tube or molded element, which provides electrical insulation and corrosion protection to the sensor chip, reduces flow noise, essentially eliminates the risk of fluid leakage, and maintains the fluid super-clean and contamination-free while improving structural integrity for the thermal measurements derived from the sensor chip. The use of such an isolated configuration also can protect the sensor from corrosion, radioactive or bacterial contamination, deposits, overheating, or freeze-ups. Such an isolated configuration also enables the flow tube and/or molded element to be detachable and disposable, without requiring the replacement of the more costly sensor chip and its associated electronics.

The flow path is precisely aligned over the sensor chip by an alignment layer that forms a location channel. The location channels can be formed on a substrate at the wafer level, providing an inexpensive, efficient means of producing multiple sensors with identically aligned flow paths.

The present invention can be used in glucose monitoring, laboratory on a chip, drug delivery, cytometer, fluid flow, dialysis, infusion, and other applications. Further, the present invention is applicable to microfluidics and flow sensing applications that need to measure liquids, condensing air or contaminated air.

The embodiments and examples set forth herein are presented to best explain the present invention and its practical application and to thereby enable those skilled in the art to make and utilize the invention. Those skilled in the art, however, will recognize that the foregoing description and examples have been presented for the purpose of illustration and example only. Other variations and modifications of the present invention will be apparent to those of skill in the art, and it is the intent of the appended claims that such variations and modifications be covered. The description as set forth is not intended to be exhaustive or to limit the scope of the invention. Many modifications and variations are possible in light of the above teaching without departing from the scope of the following claims. It is contemplated that the use of the present invention can involve components having different characteristics. It is intended that the scope of the present invention be defined by the claims appended hereto, giving full cognizance to equivalents in all respects.

We claim:

1. A method of making a plurality of flow sensors each having a flow channel aligned with a sensing element, the method comprising:
   providing a substrate having a plurality of sensing elements aligned in a pattern;
   depositing a polymer alignment layer onto the substrate;
   forming by photolithography a plurality of guide elements in the alignment layer, wherein each guide element is aligned adjacent the sensing element;
   dicing the substrate into a plurality of chips, wherein each chip has the sensing element and at least one guide element.

2. The method of claim 1, wherein the step of forming a plurality of guide elements includes depositing a polymer layer onto the substrate and forming the guide elements in the polymer layer.

3. The method of claim 2, further comprising applying a cap over the polymer layer on each chip.

4. The method of claim 2, wherein the polymer layer is a photoresist.

5. The method of claim 4, wherein the resist is poly(methyl methacrylate).

6. The method of claim 4, wherein the resist is SU-8.

7. The method of claim 1, wherein the flow channels are formed by etching.

8. The method of claim 1, wherein the substrate is selected from the group consisting of quartz, silicon, ceramic, glass, metal, and polymer.

9. The method of claim 1, wherein each guide element defines a flow channel, wherein the step of forming a plurality of guide elements includes aligning the flow channels over the sensing elements.

10. The method of claim 9, further including the step of providing a plurality of flow tubes in communication with the flow channels.

11. A method of making a plurality of flow sensors each having a flow channel aligned over a sensing element, the method comprising:
   (a) providing a substrate having a plurality of sensing elements aligned in a pattern;
   (b) depositing an alignment layer onto the substrate;
   (c) forming a plurality of guide elements in the alignment layer, wherein at least one guide element is aligned adjacent each sensing element;
   (d) dicing the substrate to form a plurality of pieces, each piece having a sensing element and at least one guide element; and
   (e) placing a molded element containing a flow channel on the guide element of each piece such that the flow channel is aligned over the sensing element.

12. The method of claim 11, wherein the guide elements are substantially the same distance from each sensing element.

13. The method of claim 11, wherein step (e) involves placing a different size flow channel on each piece to achieve a plurality of flow sensors, each having a different sized flow channel aligned over the sensing element.

14. The method of claim 11, wherein the alignment layer is a polymer and the guide elements are formed by photolithography.

15. The method of claim 11, further comprising placing a cap on the molded element, wherein the molded element forms a bottom and sides of the flow channel and the cap forms a top of the flow channel.

16. The method of claim 15, wherein the cap includes a protrusion extending into the flow channel to reduce the volume of the flow channel.

17. The method of claim 15, wherein the cap is attached to the molded element before the molded element is placed on the guide elements.

18. The method of claim 11, wherein the molded element includes a flow channel region and at least one outwardly protruding arm, wherein the at least one arm extends over the guide element and the flow channel region is aligned over the sensing element, wherein the molded element is sized such that at least a portion of a bottom surface of the flow channel contacts the substrate.

19. The method of claim 18, wherein a bottom wall of the flow channel has a thin area in contact with the substrate over the sensing element, wherein the remaining area of the bottom wall is spaced from the substrate.

* * * * *